(12) United States Patent
Foster et al.

(10) Patent No.: US 9,168,568 B2
(45) Date of Patent: Oct. 27, 2015

(54) PARTICLE MANIPULATION SYSTEM WITH CYTOMETRIC CONFIRMATION

(71) Applicant: Owl biomedical, Inc., Goleta, CA (US)

(72) Inventors: John S Foster, Santa Barbara, CA (US); Nicholas C. Martinez, Santa Barbara, CA (US); Kevin E. Shields, Santa Barbara, CA (US); Jaquelin K. Spong, Mount Jackson, VA (US)

(73) Assignee: Owl biomedical, Inc., Goleta, CA (US)

( * ) Notice: Subject to any disclaimer, the term of this patent is extended or adjusted under 35 U.S.C. 154(b) by 123 days.

(21) Appl. No.: 14/104,084

(22) Filed: Dec. 12, 2013

(65) Prior Publication Data
US 2014/0097129 A1    Apr. 10, 2014

Related U.S. Application Data

(63) Continuation-in-part of application No. 13/507,830, filed on Aug. 1, 2012.

(51) Int. Cl.
*B07C 5/34* (2006.01)
*B01L 3/00* (2006.01)
(Continued)

(52) U.S. Cl.
CPC ............ *B07C 5/34* (2013.01); *B01L 3/502761* (2013.01); *G01N 15/1404* (2013.01); *G01N 15/1434* (2013.01); *G01N 15/1459* (2013.01); *G01N 15/1484* (2013.01); *B01L 2200/0652* (2013.01); *B01L 2300/0816* (2013.01); *B01L 2400/043* (2013.01); *B01L 2400/0415* (2013.01); *B01L 2400/0439* (2013.01);
(Continued)

(58) Field of Classification Search
CPC ............... B01L 2200/0652; B01L 2200/0143; B01L 2300/0819; B01L 2300/0864; B01L 2400/0403; B01L 2400/0475; B07C 5/34; B07C 5/342; B07C 5/36; B07C 5/362; G01N 15/1404; G01N 15/1459; G01N 15/1484; G01N 2015/1415; G01N 2015/149
USPC .......... 209/210, 552, 906, 932; 422/502–505, 422/507
See application file for complete search history.

(56) References Cited

U.S. PATENT DOCUMENTS 5,304,487 A  *  4/1994  Wilding et al. ................. 435/29
5,750,015 A  *  5/1998  Soane et al. ................... 204/454
(Continued)

OTHER PUBLICATIONS

U.S. Appl. No. 13/374,899, filed Jan. 23, 2012, Foster, et al.
(Continued)

*Primary Examiner* — Joseph C Rodriguez
(74) *Attorney, Agent, or Firm* — Jaquelin K. Spong

(57) ABSTRACT

A MEMS-based particle manipulation system which uses a particle manipulation stage and a plurality of laser interrogation regions. The laser interrogation regions may be used to assess the effectiveness or accuracy of the particle manipulation stage. In one exemplary embodiment, the particle manipulation stage is a microfabricated valve, which sorts a target particle from non-target particles in a fluid stream. The laser interrogation stages are disposed in the microfabricated fluid channels at the input and output of the valve. By reversing the flow from output to input, the same laser interrogation region may be used to perform the cytometry. The cytometry may be performed throughout the sorting process to optimize or control the sorting, or may be performed afterward to allow a multi-pass, sequential sort to be performed on the same sample.

22 Claims, 15 Drawing Sheets

(51) Int. Cl.
*G01N 15/14* (2006.01)
*G01N 15/10* (2006.01)

(52) U.S. Cl.
CPC .......... *B01L 2400/0487* (2013.01); *G01N 2015/1006* (2013.01); *G01N 2015/149* (2013.01); *G01N 2015/1415* (2013.01); *G01N 2015/1438* (2013.01)

(56) References Cited

U.S. PATENT DOCUMENTS

| | | | |
|---|---|---|---|
| 5,837,200 A * | 11/1998 | Diessel et al. | 422/73 |
| 6,318,970 B1 * | 11/2001 | Backhouse | 417/92 |
| 6,736,978 B1 * | 5/2004 | Porter et al. | 210/695 |
| 6,838,056 B2 | 1/2005 | Foster | |
| 6,941,005 B2 | 9/2005 | Lary et al. | |
| 7,160,423 B2 * | 1/2007 | Chien et al. | 204/453 |
| 7,214,298 B2 | 5/2007 | Spence et al. | |
| 7,220,594 B2 | 5/2007 | Foster et al. | |
| 7,229,838 B2 | 6/2007 | Foster et al. | |
| 7,264,972 B2 | 9/2007 | Foster | |
| 7,316,320 B2 * | 1/2008 | Sibbett et al. | 209/12.2 |
| 7,389,879 B2 * | 6/2008 | Tyvoll et al. | 209/3.1 |
| 7,452,725 B2 * | 11/2008 | Leary et al. | 436/63 |
| 7,452,726 B2 * | 11/2008 | Chou et al. | 436/63 |
| 7,584,857 B2 * | 9/2009 | Bohm et al. | 209/155 |
| 7,745,221 B2 | 6/2010 | Butler et al. | |
| 2004/0233424 A1 * | 11/2004 | Lee et al. | 356/246 |
| 2013/0337500 A1 * | 12/2013 | Tan et al. | 435/39 |
| 2015/0093810 A1 * | 4/2015 | Foster et al. | 435/283.1 |

OTHER PUBLICATIONS

U.S. Appl. No. 13/374,898, filed Jan. 23, 2012, Foster, et al.

* cited by examiner

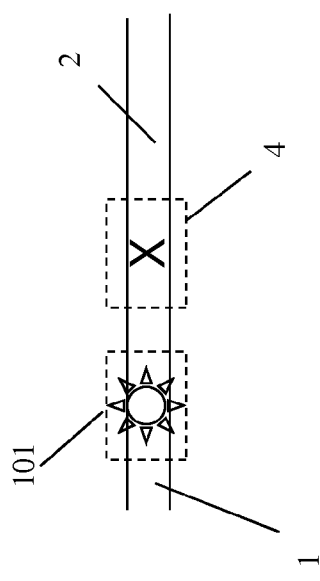
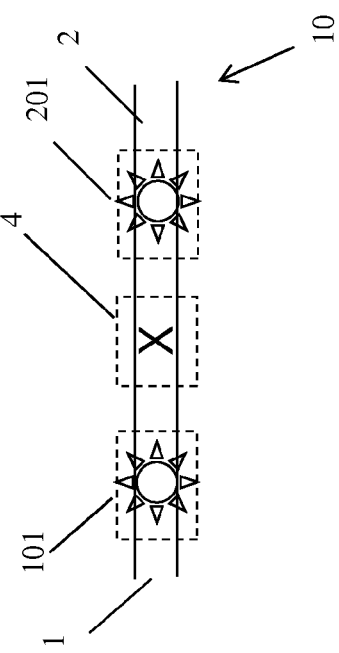

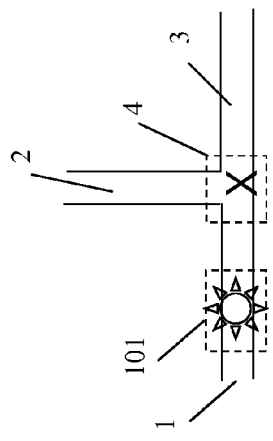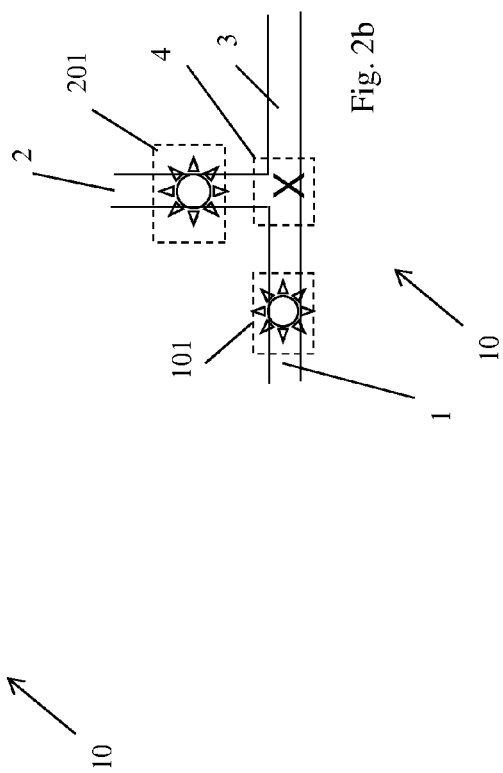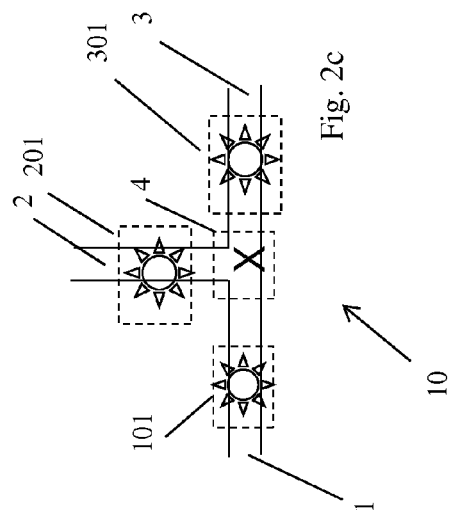

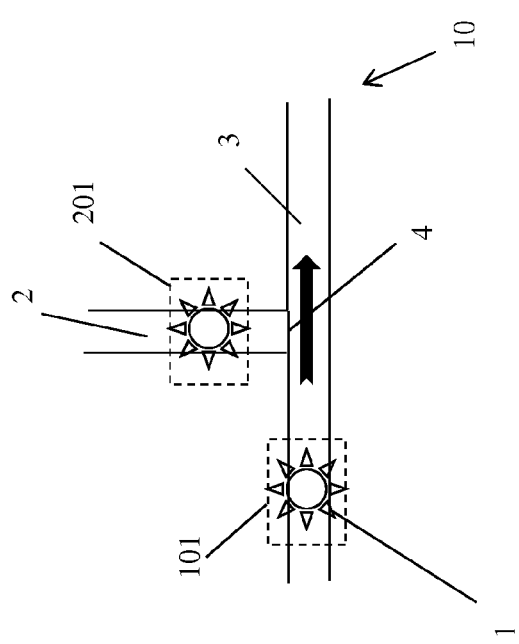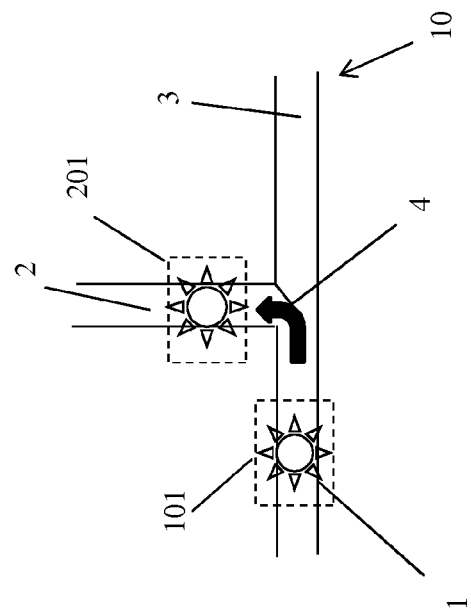

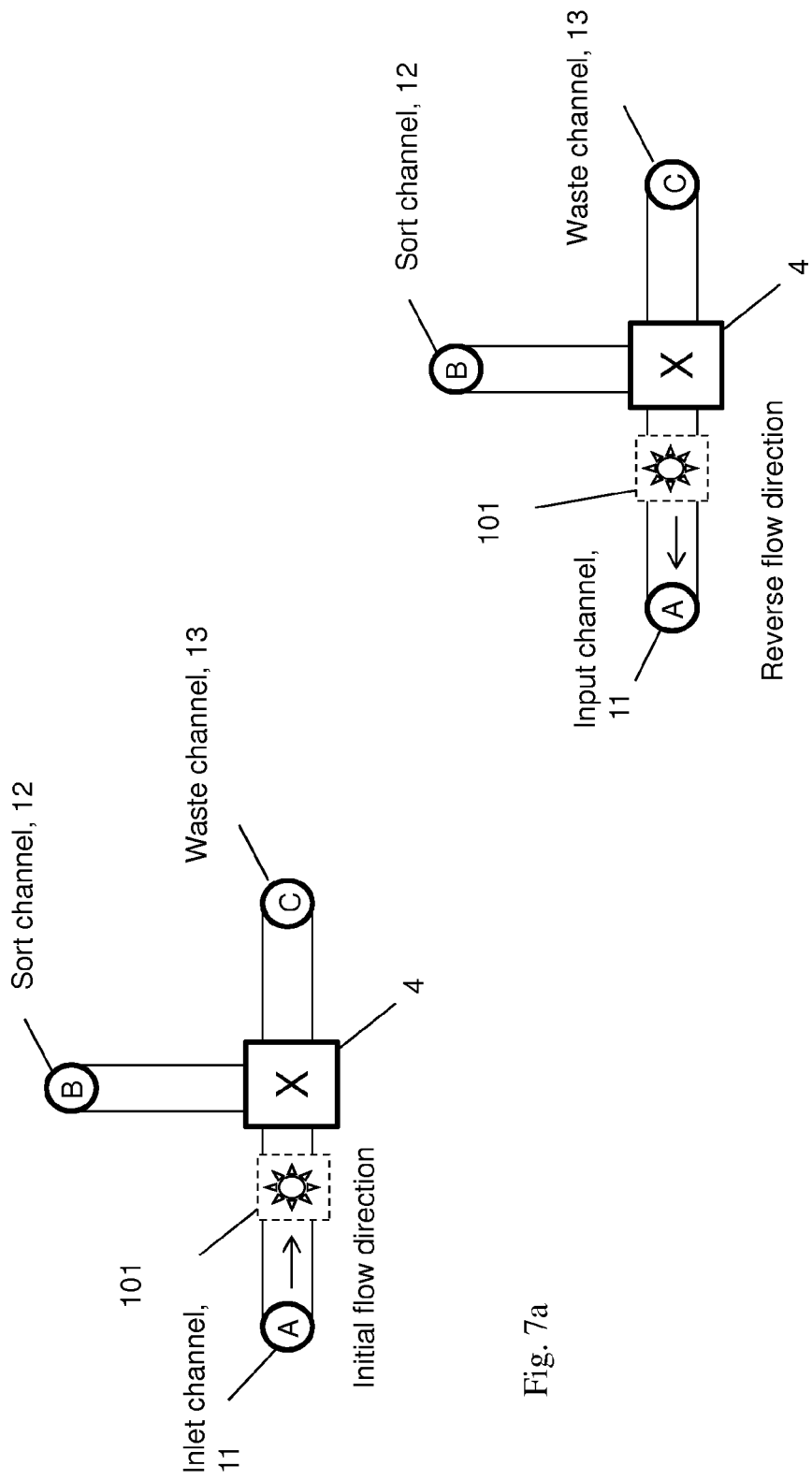

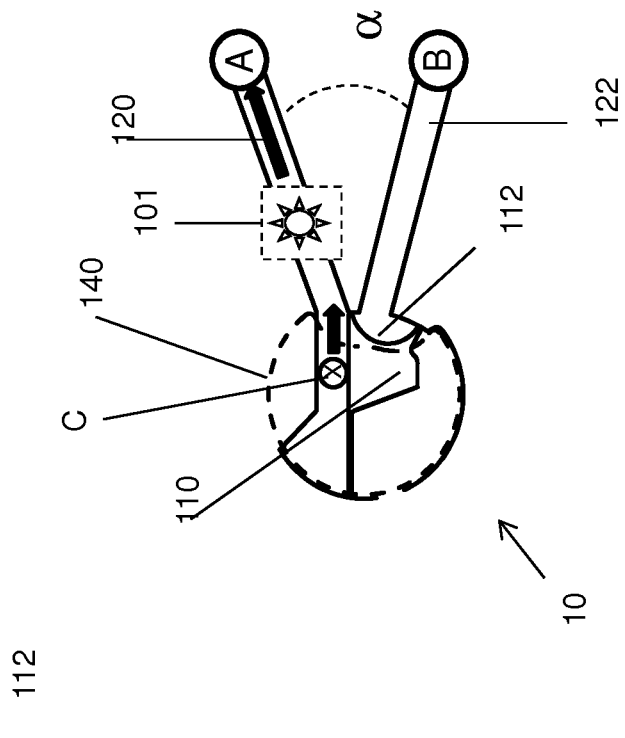
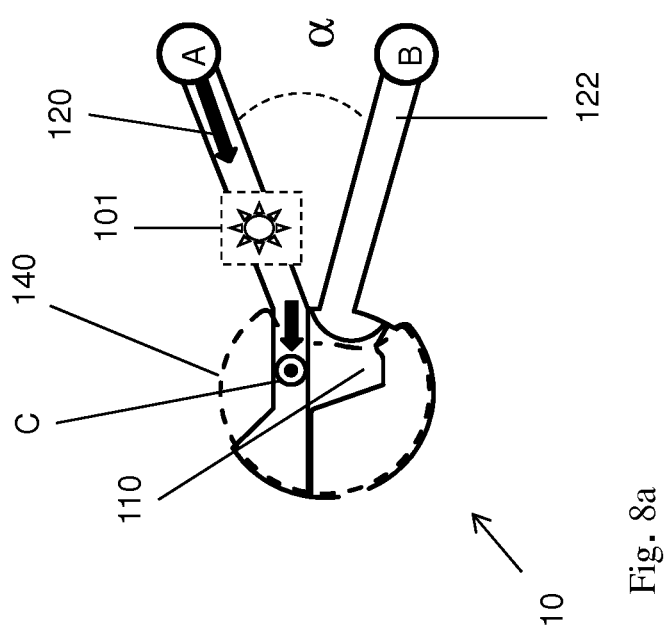
Fig. 8b
Fig. 8a

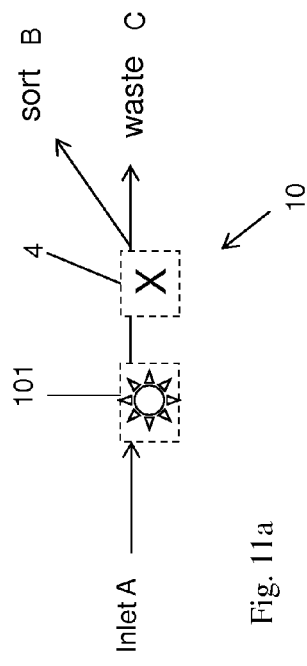
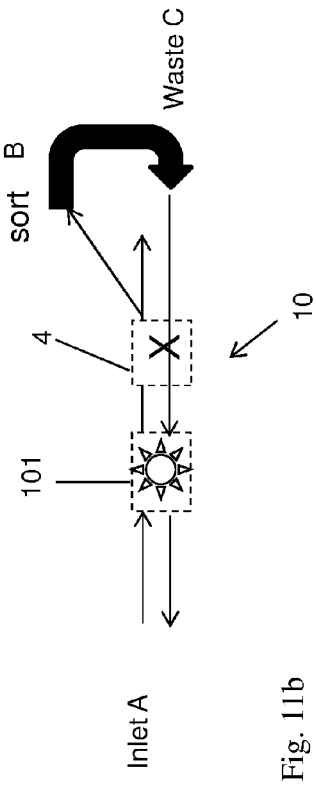
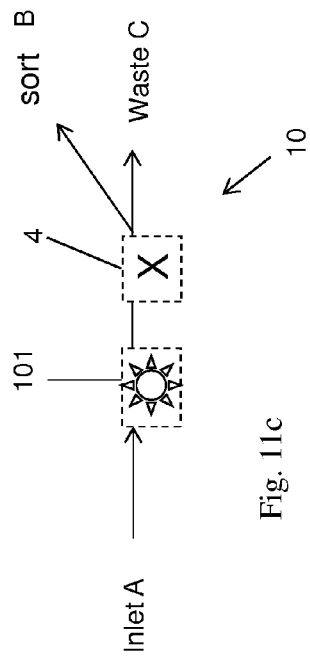

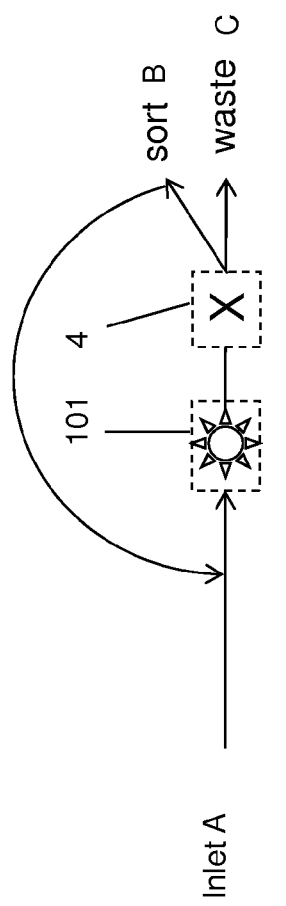
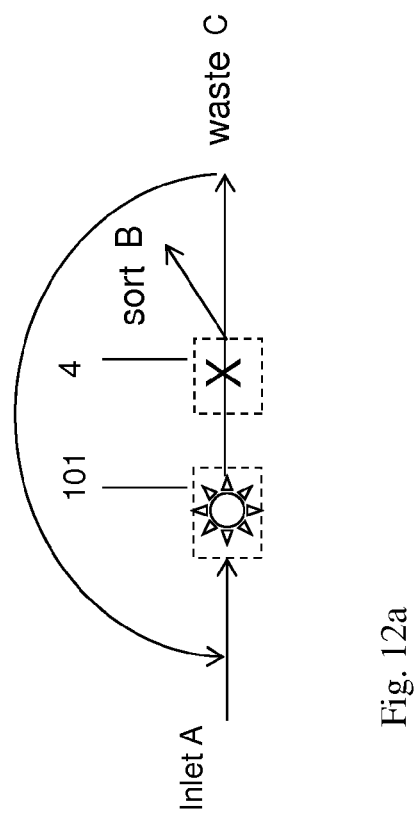

US 9,168,568 B2

PARTICLE MANIPULATION SYSTEM WITH CYTOMETRIC CONFIRMATION

CROSS REFERENCE TO RELATED APPLICATIONS

This U.S. Patent Application is a continuation-in-part of U.S. patent application Ser. No. 13/507,830, filed Aug. 1, 2012, which is incorporated by reference in its entirety. This application is related to U.S. patent application Ser. No. 13/998,095 filed Oct. 1, 2013.

STATEMENT REGARDING FEDERALLY SPONSORED RESEARCH

Not applicable.

STATEMENT REGARDING MICROFICHE APPENDIX

Not applicable.

BACKGROUND

This invention relates to a system and method for manipulating small particles in a microfabricated fluid channel.

Microelectromechanical systems (MEMS) are very small, often movable structures made on a substrate using surface or bulk lithographic processing techniques, such as those used to manufacture semiconductor devices. MEMS devices may be movable actuators, sensors, valves, pistons, or switches, for example, with characteristic dimensions of a few microns to hundreds of microns. A movable MEMS switch, for example, may be used to connect one or more input terminals to one or more output terminals, all microfabricated on a substrate. The actuation means for the movable switch may be thermal, piezoelectric, electrostatic, or magnetic, for example. MEMS devices may be fabricated on a semiconductor substrate which may manipulate particle passing by the MEMS device in a fluid stream.

For example, MEMS devices such as a movable valve, may be used as a sorting mechanism for sorting various particles from a fluid stream, such as cells from blood. The particles may be transported to the sorting device within the fluid stream enclosed in a microchannel, which flows under pressure. Upon reaching the MEMS sorting device, the sorting device directs the particles of interest such as a blood stem cell, to a separate receptacle, and directs the remainder of the fluid stream to a waste receptacle.

MEMS-based cell sorter systems may have substantial advantages over existing fluorescence-activated cell sorting systems (FACS) known as flow cytometers. Flow cytometers are generally large and expensive systems which sort cells based on a fluorescence signal from a tag affixed to the cell of interest. The cells are diluted and suspended in a sheath fluid, and then separated into individual droplets via rapid decompression through a nozzle. After ejection from a nozzle, the droplets are separated into different bins electrostatically, based on the fluorescence signal from the tag. Among the issues with these systems are cell damage or loss of functionality due to the decompression, difficult and costly sterilization procedures between sample, inability to sort sub-populations along different parameters, and substantial training necessary to own, operate and maintain these large, expensive pieces of equipment. For at least these reasons, use of flow cytometers has been restricted to large hospitals and laboratories and the technology has not been accessible to smaller entities.

A number of patents have been granted which are directed to such MEMS-based particle sorting devices. For example, U.S. Pat. No. 6,838,056 (the '056 patent) is directed to a MEMS-based cell sorting device, U.S. Pat. No. 7,264,972 (the '972 patent) is directed to a micromechanical actuator for a MEMS-based cell sorting device. U.S. Pat. No. 7,220,594 (the '594 patent) is directed to optical structures fabricated with a MEMS cell sorting apparatus, and U.S. Pat. No. 7,229,838 (the '838 patent) is directed to an actuation mechanism for operating a MEMS-based particle sorting system. Additionally, U.S. patent application Ser. No. 13/374,899 (the '898 application) and Ser. No. 13/374,898 (the '898 application) provide further details of other MEMS designs. Each of these patents and patent application publications is hereby incorporated by reference.

SUMMARY

One feature of the MEMS-based microfabricated particle sorting system is that the fluid may be confined to small, microfabricated channels formed in a semiconductor substrate throughout the sorting process. The MEMS device may be a valve which separates one or more target particles from other components of a sample stream. The MEMS device may redirect the particle flow from one channel into another channel, when a signal indicates that a target particle is present. This signal may be photons from a fluorescent tag which is affixed to the target particles and excited by laser illumination in an interrogation region upstream of the MEMS device. Thus, the MEMS device may be a particle or cell sorter operating on a fluid sample confined to a microfabricated fluidic channel, but using detection means similar to a FACS flow cytometer. In particular, the '898 application discloses a microfabricated fluidic valve wherein the inlet channel, sort channel and waste channel all flow in a plane parallel to the fabrication plane of the microfabricated fluidic valve.

A substantial improvement may be made over the prior art devices by having at least one of the microfabricated fluidic channels route the flow out of the plane of fabrication of the microfabricated valve. A valve with such an architecture has the advantage that the pressure resisting the valve movement is minimized when the valve opens or closes, because the movable member is not required to move a column of fluid out of the way. Instead, the fluid containing the non-target particles may move over and under the movable member to reach the waste channel. Furthermore, the force-generating apparatus may be disposed closer to the movable valve, resulting in higher forces and faster actuation speeds. As a result, the time required to open or close the valve may be much shorter than the prior art valve, improving sorting speed and accuracy. The systems and methods disclosed here may describe such a microfabricated particle sorting device with at least one out-of-plane channel.

A system and method are described which makes use of this architecture which is particular to the particle manipulation systems such as those disclosed in the aforementioned patents. These techniques may form a particle manipulation system with cytometric capability, as described below. A microfabricated device may be used to manipulate the particles in the fluid stream enclosed in the microfabricated channel. In this system and method, a plurality of interrogation regions exists within the microfluidic pathways, with one laser interrogation region upstream of the MEMS device, and at least one additional laser interrogation region downstream of the MEMS device. The additional laser interrogation regions may be used to confirm the performance of the microfabricated manipulation device.

Accordingly, the particle manipulation system with cytometric capability may include laser light directed into a first laser interrogation region in first portion of a microchannel formed in a substrate, at least one particle manipulation stage formed in the substrate, and laser light directed into at least one additional laser interrogation region formed in a second portion of a microchannel formed in the substrate, wherein the first portion of the microchannel is disposed upstream of the particle manipulation stage, and the second portion of the microchannel is disposed downstream of the particle manipulation stage, and the particle manipulation stage comprises a movable structure microfabricated on the substrate which includes the microfluidic channels.

In one embodiment, the MEMS device is a microfabricated valve having at least one of the microfabricated fluidic channels flowing out of the plane of fabrication of the microfabricated valve. The valve may sort a target cell (cancer cell, sperm cell, stem cell for example) from the other components of a fluid stream. The MEMS valve may be actuated into the channel to redirect the flow in response to the detection of a target particle in the channel. The valve directs the flow into a sort channel rather than a waste channel.

In one embodiment, the additional interrogation region may be disposed in the sort channel, where the target particles are directed by the MEMS sorter. By counting the proportion of target particles to non-target particles, the effectiveness of the sorter can be ascertained, and properties or parameters can be adjusted as the sorting process is underway.

In another embodiment, the additional interrogations take place using the same laser interrogation region, by passing the column of fluid through the same laser interrogation region multiple times. The additional interrogation can be performed on the sorted output, or the waste output, or both. The additional interrogations may be performed intermittently throughout the sort, to adjust the sorting parameters, or they may take place at the end of the sort to measure the sort purity and yield. The sort can also be performed multiple times on essentially the same volume of fluid, so as to improve the sort purity and/or yield.

The reverse-flow cytometric confirmation process may be particularly suited to the out-of-plane type of microfabricated valve, as mentioned above. In particular, it has been determined that a microfabricated valve with at least one output channel being disposed out-of-the plane of the sample inlet channel and one other in-plane output channel, may have substantially lower turbulence and reduced resistance to fluid flowing backwards through the device. This applies to both reverse-flow confirmation of the sort and non-sort fraction. The reduced turbulence during valve actuation relative to other actuators, such as that described in the '898 application, may reduce the likelihood of sorting errors while reversing flow direction in the sort channel. Because of its low resistance to fluid flow, the reverse flow and interrogation may be performed more quickly, and so with less processing overhead than other valve architectures. Accordingly, such an architecture may be particularly advantageous for implementation of the concepts described here.

Accordingly, a microfabricated particle sorting system is described, comprising a sample inlet channel, a sort channel and a waste channel in fluid communication and formed in the surface of a substrate, wherein the flow in the sample inlet channel is substantially parallel to the surface; wherein the flow in at least one of the sort channel and the waste channel is not parallel to the plane, and wherein the sample channel flows to at least one of the sort channel and the waste channel when a flow is forward. The particle sorting system may also include an interrogation means disposed in the sample channel, wherein a target particle provides a detection signal, and a microfabricated particle sorting mechanism formed at a junction of the sort channel and waste channel, which moves to direct the target particle from the sample channel into the waste channel when the particle sorting mechanism is in a first position, and which directs the other particles into the sort channel when in a second position, wherein at least one of the sort channel and the waste channel is located directly below or above at least a portion of the microfabricated particle sorting mechanism over at least a portion of its motion. The particle sorting system may also include a means for reversing the flow from at least one of the sort stream and the waste stream back to the sample stream, and back through the laser interrogation region and the particle manipulation stage.

These and other features and advantages are described in, or are apparent from, the following detailed description.

BRIEF DESCRIPTION OF THE DRAWINGS

Various exemplary details are described with reference to the following figures, wherein:

FIG. 1a is a simplified illustration of a microfabricated particle manipulation system;

FIG. 1b is a simplified illustration of a microfabricated particle manipulation system according to the present invention;

FIG. 2a is a simplified illustration of a microfabricated particle manipulation system having an intersection;

FIG. 2b is a simplified illustration of a microfabricated particle manipulation system having an intersection according to one embodiment of the present invention;

FIG. 2c is a simplified illustration of a microfabricated particle manipulation system having an intersection according to another embodiment of the present invention;

FIG. 3a is a simplified illustration of a microfabricated particle sorting system according to one embodiment of the present invention, with the sort valve in the closed position;

FIG. 3b is a simplified illustration of a microfabricated particle sorting system according to one embodiment of the present invention, with the sort valve in the open position;

FIG. 7a is a schematic view of a particle sorting system in the forward flow direction; FIG. 7b is a schematic view of a particle sorting system in the backward flow direction;

FIG. 8a is a simplified plan view of a microfabricated particle sorting system in the quiescent (no sort) position and with forward flow and positive pressure as shown in FIG. 7a; FIG. 8b is a simplified plan view of a microfabricated particle sorting system in the quiescent (no sort) position and with backward flow and reverse pressure as shown in FIG. 7b;

FIG. 9a is a simplified plan view of a microfabricated particle sorting system in the actuated (sort) position and with forward flow and positive pressure as shown in FIG. 7a.

FIG. 11a is a schematic view of a particle sorting system performing a forward sort procedure; FIG. 11b is a schematic view of a particle sorting system performing a reverse cytometric confirmation from the sort reservoir; FIG. 11c is a schematic view of a particle sorting system performing a forward sort procedure using parameters from the confirmation;

FIG. 12a is a schematic view of a particle sorting system performing a serial sort from the waste reservoir; FIG. 12b is a schematic view of a particle sorting system performing a serial sort from the sort reservoir;

DETAILED DESCRIPTION

Figure 4A:
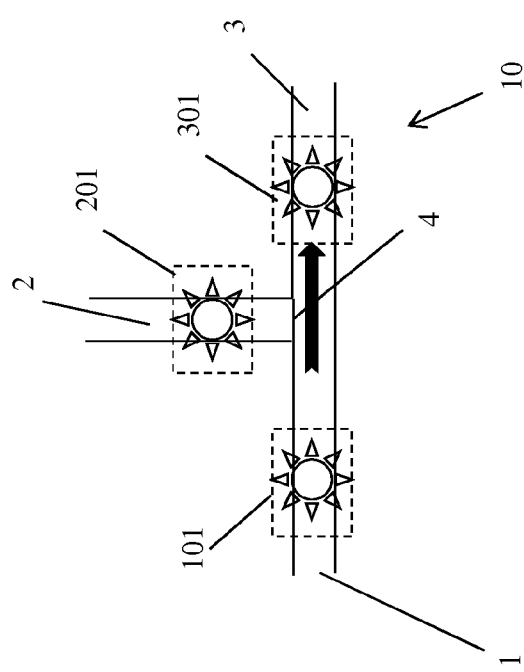
FIG. 4a is a simplified illustration of a microfabricated particle sorting system according to another embodiment of the present invention, with the sort valve in the closed position.

The system described herein is a particle sorting system which may make use of microchannel architecture of a particle manipulation system, such as those disclosed in the aforementioned patents. More generally, the systems and methods describe a particle manipulation system with multiple passes through a laser interrogation region, which form a particle manipulation system with cytometric capability. The multiple laser interrogation regions may provide information as to the effectiveness or accuracy of the particle manipulations, allowing the manipulations to be adjusted or controlled during the process.

In the figures discussed below, similar reference numbers are intended to refer to similar structures, and the structures are illustrated at various levels of detail to give a clear view of the important features of this novel device.

FIG. 1a is a schematic illustration of a MEMS-based particle manipulation system using lithographically formed microfluidic channels. One microfluidic channel 1 may be an inlet channel which directs a fluid flow. The fluid stream in microfluidic channel 1 flows through a first laser interrogation region 101. In this region, light from one or more lasers is directed. The light may be focused to a spot and onto the particles flowing in the stream, wherein the laser interrogation region 101 is disposed upstream of a microfabricated manipulation stage 4. If the particles have the appropriate fluorescent tag affixed thereto, the tag may be excited and emit a characteristic fluorescent photon. This photon may be detected by optical detectors and evaluated by appropriate logic circuits. The logic circuits may control the manipulation stage 4, which may manipulate the tagged particles under the control of the logic circuits.

In one exemplary embodiment, the MEMS device may apply a charge to the target particle. In another exemplary embodiment discussed further below, the manipulation stage 4 may be an actuator, which diverts the target particle into a different flow path as the non-target particles.

FIG. 1b is a schematic illustration of a particle manipulation system with cytometric capability 10, which uses lithographically formed microfluidic channels, according to the present invention. One microfluidic channel 1 may be an inlet channel which directs a fluid flow into a manipulation stage 4. Microfabricated device 4 may alter the trajectory, morphology, shape, charge or other characteristic of the particle. Another microfluidic channel 2 directs the fluid flow away from the manipulation stage 4 and into an output channel. A second laser interrogation region 201 may be positioned in microfluidic channel 2. Using laser interrogation region 201 to interrogate the passing particles, the effectiveness, accuracy and/or efficiency of MEMS manipulation stage 4 can be assessed. The simultaneous detection of fluorescence and the manipulated characteristic indicates accurate performance of the manipulation stage.

For example, manipulation stage 4 may apply a charge to a passing particle. Laser interrogation stage 201 may confirm the presence of both the charge and the fluorescent tag by measuring the voltage on a parallel plate capacitor (not shown) installed in the channel 2. By so doing, the coincidence of both the fluorescence and the voltage signal is evidence that the charge is correctly placed on tagged particles. In the case of a particle or cell sorter, the presence of the target sorted particle in the sort passage where the additional laser interrogation stage 201 is placed, may indicate correct and effective sorting.

FIG. 2a is a schematic illustration of another particle manipulation system with cytometric capability, using lithographically formed microfluidic channels. In FIG. 2a, two or more channels are formed at the output of the manipulation stage 4, forming an intersection point. One channel 2 may move in one path away from the manipulation stage 4, whereas another channel 3 may move in another path away from manipulation stage 4. FIG. 2b depicts another particle manipulation system with cytometric capability. As shown in FIG. 2b, channel 2 may be equipped with an additional laser interrogation stage 201, which may identify the various particles according to their response to irradiation with laser light. If a particle emits a photon in response to irradiation, that is an indication that it is a tagged, target particle. If it does not, it is likely an untagged, non-target particle.

As shown in FIG. 2c, both channels 2 and 3 may be equipped with an additional laser interrogation stage 201 and laser interrogation stage 301, which may identify the various particles according to their response to irradiation with laser light. Indeed, any number of additional laser interrogation regions may be placed in any number of microfluidic channels, although large numbers of such regions may become difficult to separate, as described more fully below. As before, if a particle emits a photon in response to irradiation, that is an indication that it is a tagged, target particle. If it does not, it is likely an untagged, non-target particle. These two laser interrogation stages may measure the difference in density of target particles in one channel 2 relative to the other channel 3 or inlet channel 1.

FIG. 3a is a schematic illustration of a particle manipulation system with cytometric capability 10 using multiple laser interrogation regions disposed in lithographically formed microfluidic channels. The manipulation stage 4 may be a MEMS flap-type actuator or sorter. The MEMS flap-type actuator is shown schematically in FIG. 3a, and may be a flap-type fluidic valve which separates a target particle from a remainder of the sample stream, based on a signal from the first laser interrogation region. The MEMS flap-like actuator may be a simple, hinge mounted movable member that may be drawn downward in response to a force acting on the movable member. The force may be, for example, electrostatic, magnetostatic or electromagnetic. The movable member may be formed lithographically on a silicon substrate, and methods for manufacturing such a device may be found in the above-incorporated patents and patent applications.

The MEMS actuator may divert the incoming fluid stream into one of the plurality of exit channels, for example into either channel 2 or channel 3. For example, if a signal from laser interrogation region 101 indicates that a target particle is present, the logic circuit coupled to laser interrogation region 101 may send a signal to the MEMS actuator 4 to activate the flap. Drawing down the flap will divert the detected target particle into the sort channel 2 rather than allowing it to flow past into waste channel 3.

Figure 4B:
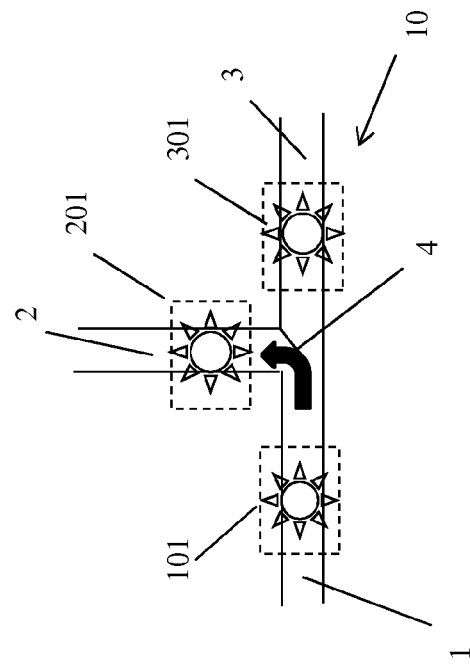
FIG. 4b is a simplified illustration of a microfabricated particle sorting system according to another embodiment of the present invention, with the sort valve in the open position.

As mentioned previously, waste channel 3 may also be equipped with an additional laser interrogation region 301. This arrangement is shown in FIGS. 4a and 4b, which are similar to FIGS. 3a and 3b, except that two laser interrogation regions 201 and 301 are disposed in sort channel 2 and waste channel 3, respectively. The two additional interrogation regions 201 and 301 may measure the increased density of target cells in sort channel 2 compared to waste channel 3, and thus may provide evidence of the effectiveness and accuracy of the MEMS particle manipulation stage (sorter) 4 and laser interrogation region 101.

Thus, as can be seen from the figures above, the additional laser interrogation regions 201 and 301 (or more) may act as a cytometer or as a quality control measure. The system 10 may give feedback as to the correct setting of any adjustable parameters in the sorting algorithm. Such parameters may include, for example, fluorescent pulse shape, width, magnitude or duration, laser intensity, optical alignment or focusing. These parameters may then be adjusted during the sort, rather than waiting for the entire sample to be processed before finding a problem in the sorting. The presence of additional laser interrogation regions 201 and/or 301 may provide cytometer capability to the sorter, in that it is able to count, enumerate, or quantify the density or purity of the sorted sample, while the sorting process is underway. This capability may allow the sort process to be adjusted in real time, that is, while it is underway. This may allow an optimization of sort parameters without performing multiple sorting operations on a sample, thus saving time and sample volume.

Figure 5:
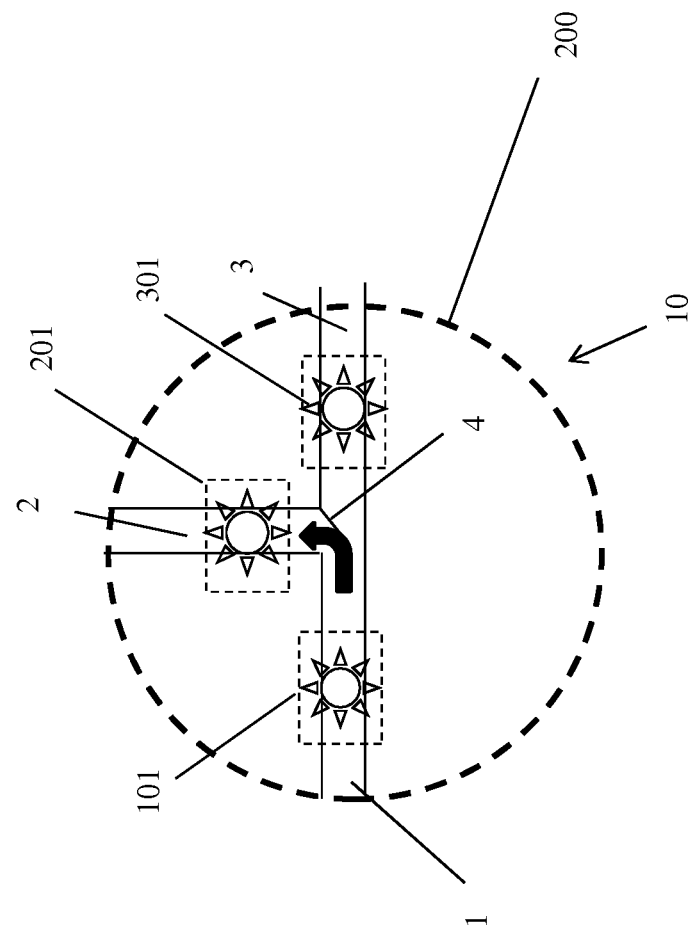
FIG. 5 is a simplified illustration of a microfabricated particle sorting system according to an embodiment of the present invention, showing the field of view of the detector compared to the interrogation regions.

Also shown in FIG. 5 is the field of view 200 of the detector monitoring laser interrogation region 101 as well as additional laser interrogation regions 201 and 301. As indicated in FIG. 5, all laser interrogation regions may fall within the detector field of view, and thus may share at least a portion of the optical and electronic data detection channel. Accordingly, light collected from the at least one additional laser interrogation region is collected by an optical system which also collects light from the first laser interrogation region. Details as to how to exploit or implement this feature are set forth below with respect to the remaining figures.

As was shown in FIG. 5, the approximate field of view of the detection optics may cover all laser interrogation regions 101, 201 and 301, as described in greater detail below. Of note in FIG. 5, since the field of view of the detection optics is sufficiently large to include laser interrogation region 101, as well as laser interrogation region 201, and even laser interrogation region 301, or more, the multiple laser interrogation regions may share at least a portion of an optical detection path. This is a result of the small scale of the microfabricated cell sorter and associated microfluidic channels. Each of the channels 1, 2 and 3 is on the order of 20 microns in width. The distance between laser interrogation region 1 and MEMS particle manipulation mechanism 4 may be kept below 500 microns or so, in order to reduce the timing uncertainty between the passage of the target particle and the opening of the MEMS particle manipulation mechanism 4. As this distance gets longer, the additional uncertainty may mean that a non-target particle is allowed into the sort channel 2, or a target particle is allowed to pass into waste channel 3. Either of these events reduces the purity or the yield of the sorted sample. Accordingly, to optimize the sort performance, the distance between the detection region and the sorter may be kept as short as practical.

While the particle manipulation in this embodiment is a cell sorter, it should be understood that any number of particle manipulations may be performed, such as tagging, charging, heating, altering and destroying rather than sorting.

In general, the valves, actuators or manipulators 4 used herein may be formed on a semiconductor substrate using lithographic techniques well known in MEMS fabrication. Details of their fabrication techniques may be found in the aforementioned patents. Thus, a characteristic dimension, for example its total width or length of the structure may be about 500 microns or less, and the fluidic channels may be formed in the same substrate with characteristic dimensions of about 10-20 microns.

For the same reason, the laser interrogation regions 2 and 3 should also be located ideally near the manipulation stage 4 as well. These considerations lead to the small dimensions of the structure, and these dimensions are also well suited to lithographic processing methodologies as described in the incorporated patents and patent applications.

However, the result of these dimensions is that the additional laser spots fall into the same field of view, and therefore may be processed by the same optical channel. Accordingly, measures may be taken to separate the data falling in the same optical channel but emanating from different laser interrogation regions. These measures may include altering the trajectory, spectral content, timing and/or duration of the laser energy directed into these additional laser interrogation regions. Alternatively, separate laser sources and detection optics may be provided. Various embodiments of achieving this separation are described more fully below.

Figure 6:
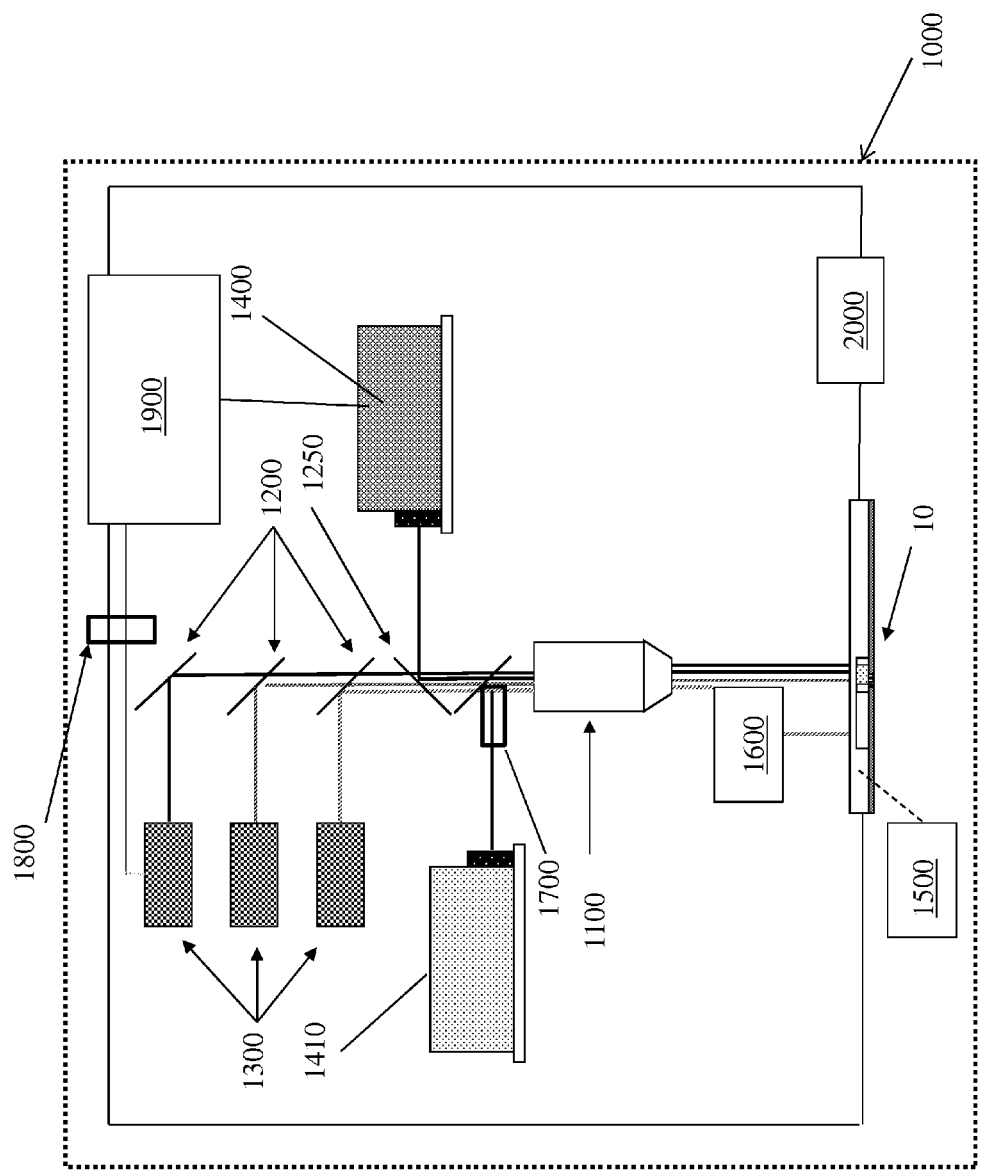
FIG. 6 is a simplified system-level illustration of a microfabricated particle sorting system according to the present invention, showing the placement of the various optical components.

FIG. 6 is a schematic illustration of the particle manipulation system 1000 using multiple laser interrogation regions as described above. In particular, FIG. 6 lays out the optical path of the interrogating laser and detection optics.

In one embodiment of system 1000, the target particle may be a particular cell, such as a stem cell, or a cancer cell, which has been tagged with a fluorescent marker. This marker emits photons having a particular energy when irradiated with a laser 1400 operating at a predefined wavelength. Accordingly, in this cell sorting system, a laser source 1400 may be directed by a turning mirror 1250 through the detection/collection optics 1100 onto the MEMS particle manipulation mechanism 4 in the detection region 101 shown in FIG. 1. The optical axis of the detection/collection optics 1100 and the laser source 1400 may be collinear, at least over a portion of the optical path. Thus, the orientation of the laser application and optical detection along this optical axis may be perpendicular or orthogonal to the substrate fabrication plane, orthogonal to the plane of motion of the sorter flap movable structure 4 and orthogonal to the flow of the sample fluid through the detection region. This may have important consequences as the light traverses the surfaces with an orthogonal angle of incidence, which may reduce specular reflection and thus reduce or eliminate a noise source in the detection scheme.

The fluorescence emitted from the irradiated particles may be shaped by detection/collection optics 1100 and separated by dichroic minors 1200 and directed into a bank of photodetectors 1300. A plurality of photodetectors may accommodate multiple wavelengths of emitted light, for multiparametric detection. The signal output by the photodetectors 1300 indicates the presence or absence of the target particle in the detection region 101. The signal may be delivered to a controller 1900, which manages the relative timing of the components in the particle sorting system 1000, and collects the data. The controller 1900 may be a general purpose computer or a specialized circuit or ASIC. Upon detection of the target particle, a signal is generated by the controller 1900 which energizes the force-generating or flux-generating apparatus 1500. The controller 1900 may also provide the fluidic control to the particle manipulation device 10, via one or more pneumatic, hydraulic, piston-based or mechanical force-based mechanisms.

The force generating apparatus 1500 is a device which causes a force to arise in the MEMS particle manipulation mechanism 4 itself, causing the motion of the movable structure. This force-generating apparatus 1500 may not be directly mechanically coupled to the MEMS particle manipulation mechanism 4, as indicated by the dashed line in FIG. 6. For example, the force-generating apparatus 1500 may be a source of magnetic flux which causes a magnetostatic force to arise in an inlaid permeable material in the MEMS particle manipulation mechanism 4. Accordingly, flux generating apparatus 1500 may be an electromagnet with a magnetic core and windings. This force may pull the flap or movable structure 4 toward the force-generating apparatus 1500, opening the sort channel 2 and closing the waste channel 3, as was shown in FIGS. 3-5. Importantly, the force-generating apparatus 1500 may reside in the particle sorting system 1000, rather than in the MEMS particle manipulation mechanism 4. As mentioned previously, this may reduce the cost and complexity of the MEMS particle manipulation mechanism 4. Another optional laser 1410 may also be included to provide a second optical channel.

In the detection region 101, the target particle may be distinguished from the other constituents of the fluid sample. The detection means may be, but is not necessarily, a laser 1400 and associated optics, which directs the laser to a spot upstream of the MEMS particle manipulation mechanism 4, and generally in detection region 101. The detection means may be based on any number of characteristics or attributes that distinguish the target particle from the others in the fluid stream. For example, the particles may be distinguished by, for example, differences in an electrical attribute, a hydrodynamic attribute, a magnetic attribute, an optical attribute, a thermal attribute, mass, and a mechanical attribute of the particle, to name just a few. This list is not meant to be exhaustive, but instead to provide examples of detection systems which may be used with the actuator described herein.

In one embodiment, the target particle may be a particular cell which may be tagged with a fluorescent tag, which emits light of a particular color when irradiated by a laser at a particular wavelength. Such tags are well known in the field and include for example fluorescein, Texas Red, phycobiliproteins, cyanine derivatives and rhodamine. While much of this disclosure is directed to this application, it should be understood that the systems and methods described herein are also applicable to other detection mechanisms used to distinguish particles one from another. These mechanisms may be well known, or may yet be invented.

Upon passing through the detection region 101, a signal is generated by the detector 1300 indicating that a target particle is present in the first interrogation region 101. After a known delay, a signal is generated by the controller 1900 which indicates that the sorting gate, i.e. the movable diverter, or MEMS particle manipulation stage 4, is to be opened, in order to separate the target particle which was detected, from the other components in the fluid stream. The movable diverter or MEMS particle manipulation mechanism 4 may comprise permeable magnetic materials, so that the magnetic force may arise between them when the magnetic field is present. When the signal is generated by the controller 1900, a force is generated between the embedded magnetically permeable material in the diverter or MEMS particle manipulation mechanism 4, which draws the diverter or MEMS particle manipulation mechanism 4 toward the force generating apparatus 1500. This motion closes off waste channel 3 and redirects the target particle into a sort channel 2. The sorted sample is subsequently collected from a sort reservoir at the end of the sort channel 2 or 46, which holds the sorted sample.

The microfabricated particle manipulation system 10 may be inserted into a housing containing the components shown in FIG. 6. The insertion area may be a movable stage with mechanisms available for fine positioning of the particle manipulation device 10 and associated microfluidic channels against one or more data, which orient and position the detection region and particle manipulation device 10 with respect to the detection/collection optics 1100. If finer positioning is required, the input stage may also be a translation stage, which adjusts the positioning based on observation of the location of the movable diverter or MEMS particle manipulation mechanism 4 relative to the datum.

A pressure control means 2000 may control the direction and velocity of fluid flowing through the channels of the microfabricated particle manipulation system 10. The flow may be controlled based on a number of criteria as described further below, via pneumatic, hydraulic, and/or one way valves, and may include a piston with a pump and associated fluidic passages. The flow may be controlled in a feedback loop by controller 1900 to keep fluid velocity, pressure, or event rate constant, for example.

The MEMS particle sorting system 1000 shown in FIG. 6 may include a number of elements that may be helpful in implementing the additional interrogation regions 201 and 301, or more. First, an optical manipulating means 1600 may alter the trajectory, spectral content, timing or duration of the laser radiation from laser 1400 to the second or third interrogation spots. Examples of items that may be included in optical manipulating means 1600 are a birefringent crystal, spinning prism, mirror, saturable absorber, acousto-optic modulator, harmonic crystal, Q-switch, for example. More generally, optical manipulating means 1600 may include one or more items that alter laser frequency, amplitude, timing or trajectory along one branch of the optical path to an additional interrogation region.

For example, optical manipulating means 1600 may include a beamsplitter and photoacoustic modulator. The beam splitter may separate a portion of the incoming laser beam into a secondary branch or arm, where this secondary branch or arm passes through the modulator which modulates the amplitude of the secondary beam at a high frequency. The modulation frequency may be, for example, about 2 MHz or higher. The light impinging on the first laser interrogation region 101 may, in contrast, be continuous wave (unmodulated). The secondary branch or arm is then directed to the additional laser interrogation region 201 or 301. This excitation will then produce a corresponding fluorescent pattern from an appropriately tagged cell.

This modulated fluorescent pattern may then be picked up by the detection optics 1600, which may recombine the detected fluorescence from interrogation region 201 and/or 301 with fluorescence from laser interrogation region 101. The combined radiation may then impinge on the one or more detectors 1300.

An additional optical component 1700 may also alter the frequency, amplitude, timing or trajectory of the second beam path, however, it may perform this operation upstream (on the detector side) of the detection/collection optics 1100 rather than downstream (on the sample side) of it, as does optical component 1600.

The output of detectors 1300 may be analyzed to separate the content corresponding to region 201 and/or region 301 from the content corresponding to laser interrogation region 101. This may be accomplished by applying some electronic distinguishing means to the signals from detectors 1300. As shown in FIG. 6, the electronic distinguishing means 1800 may include electronic circuitry that distinguishes the signals coming from laser interrogation region 101 from those of laser interrogation regions 201 and/or 301. The details of electronic distinguishing means 1800 may depend on the choice for optical manipulation means 1600. For example, a filter may include a high pass stage and a low pass stage that is consistent with the photoacoustic modulator.

As should be clear from the above discussion, the system implementing the cytometric capability in a separate laser interrogation region 201 or 301 has a number of elements needed to separate the signal coming from laser interrogation region 101 from laser interrogation region 201 or 301. In particular, elements 1600, 1700 and 1800 are included in the system in order to distinguish the signals coming from different laser interrogation regions. In another embodiment however, the very same laser interrogation region 101 may be used to subsequently assess the quality of the particle manipulation, as is described further below. In this embodiment, each of the multiple cytometric measurements takes place separated in time, rather than in space. Each subsequent cytometric capability may use the exact same laser interrogation region 101.

It should be understood that laser interrogation region 101 may in fact include several laser spots which arise from one or more lasers, and indeed the interrogation need not be a laser at all, but some other distinguishing means based on some other optical, mechanical, or electrical differences for example, as is known in the art of cytometry. As described further below, the distinguishing means may be scattered light or side scattered light which may be based on the morphology of a particle, or may be any number of mechanical, chemical, electric or magnetic effects that can identify a particle as being either a target particle.

FIGS. 7a and 7b show a system which is conceptually similar to the system shown in FIGS. 2a and 2b. However, in FIGS. 7a and 7b, the pump mechanism is shown as pressure sources A, B and C. A pressure source A provides a fluid pressure to sample inlet channel 11, which drives a sample fluid through laser interrogation region 101 and MEMS particle manipulation mechanism 4. MEMS particle manipulation mechanism 4 directs the stream into either the sort channel 12 or waste channel 13. A pressure source B provides a fluid pressure to sort channel 12. A pressure source C provides a fluid pressure to the waste channel 13. As long as A>B and A>C, the fluid will flow to either the sort channel or the waste channel, depending on the position of the MEMS particle manipulation mechanism 4. It should be understood that microfluidic channels 11, 12 and 13 may each lead to respective inlet, sort and waste reservoirs, which can store a volume of fluid. The designations A, B and C may refer to either this reservoir, or the pressure applied to the reservoir through a pumping means. This volume in the reservoirs A, B, and C may be on the order of 10-30 ml, and the entire system of microfluidic channels, reservoirs, MEMS valve and interrogation region may be contained in a removable, disposable cartridge, as described for example in U.S. patent application Ser. No. 13/374,899, filed Jan. 23, 2012 and incorporated by reference.

However, if C>A or B>A, the fluid stream will flow backward from the waste channel 13 to sample inlet channel 11, or from sort channel 12 back to sample inlet channel 11, depending on the position of the MEMS particle manipulation mechanism 4. This situation is shown in FIG. 7b. Using such a system, fluid from the sort reservoir B or waste reservoir C can be made to pass again through laser interrogation region 101. As will be described further below, this subsequent pass through interrogation region 101 can be used to confirm the contents of the sort or waste reservoirs B or C.

FIG. 8a shows in plan view one embodiment of a novel particle manipulation device 10 which can be used with the system shown in FIGS. 7a and 7b. Novel particle manipulation device 10 is described in greater detail in U.S. patent application Ser. No. 13/998,095 (the '095 application), filed Oct. 1, 2013 and assigned to the same assignee as the present application. The '095 application is incorporated by reference in its entirety. The device 10 is in the quiescent (un-actuated) position. The device 10 may include a microfabricated fluidic valve or movable member 110 and a number of microfabricated fluidic channels 120, 122 and 140. The fluidic valve 110 and microfabricated fluidic channels 120, 122 and 140 may be formed in a suitable substrate, such as a silicon substrate, using MEMS lithographic fabrication techniques as described in greater detail below. The fabrication substrate may have a fabrication plane in which the device is formed and in which the movable member 110 moves.

A sample stream may be introduced to the microfabricated fluidic valve 110 by a sample inlet channel 120 from sample reservoir A. The sample stream may contain a mixture of particles, including at least one desired, target particle and a number of other undesired, nontarget waste particles. The particles may be suspended in a fluid. For example, the target particle may be a biological material such as a stem cell, a cancer cell, a zygote, a protein, a T-cell, a bacteria, a component of blood, a DNA fragment, for example, suspended in a buffer fluid such as saline. The inlet channel 120 may be formed in the same fabrication plane as the valve 110, such that the flow of the fluid is substantially in that plane. The motion of the valve 110 is also within this fabrication plane. The decision to sort/save or dispose/waste a given particle may be based on any number of distinguishing signals. In one exemplary embodiment, the decision is based on a fluorescence signal emitted by the particle, based on a fluorescent tag affixed to the particle and excited by an illuminating laser. Details as to this detection mechanism are well known in the literature. However, other sorts of distinguishing signals may be anticipated, including scattered light or side scattered light which may be based on the morphology of a particle, or any number of mechanical, chemical, electric or magnetic effects that can identify a particle as being either a target particle, and thus sorted or saved, or an nontarget particle and thus rejected or otherwise disposed of.

With the valve 110 in the position shown, the inlet stream passes unimpeded to an output orifice and channel 140, which may be out of the plane of the inlet channel 120, and thus out of the fabrication plane of the particle manipulation device 10. This direction is indicated by reference C in FIG. 9a, which is analogous to C in FIGS. 7a and 7b. That is, the flow is from the inlet channel 120 and sample inlet reservoir A to the output orifice 140, from which it flows substantially vertically C into output orifice 140. The flow C is thus substantially orthogonal to the inlet channel 120, and thus substantially orthogonal to the fabrication plane and the plane of motion of particle manipulation device 10. The flow C into output orifice 140 may therefore be perpendicular to the plane of the paper. More generally, the output channel 140 may not be parallel to the plane of the inlet channel 120 or sort channel 122, or the fabrication plane of the movable member 110.

The output orifice 140 may be a hole formed in the fabrication substrate, or in a covering substrate that is bonded to the fabrication substrate. A relieved area above and below the sorting valve or movable member 110 allows fluid to flow above and below the movable member 110 to output orifice 140. Further, the valve 110 may have a curved diverting surface 112 which can redirect the flow of the inlet stream into a sort output stream. The contour of the orifice 140 may be such that it overlaps some, but not all, of the inlet channel 120 and sort channel 122. By having the contour 140 overlap the inlet channel, and with relieved areas described above, a route exists for the inlet stream to flow directly into the waste orifice 140 when the movable member or valve 110 is in the un-actuated waste position.

The device shown in FIG. 8a is designed to transport nominally 4 ml of fluid/hour from sample inlet source A to waste orifice C when the valve is in the position shown in FIG. 8a, and forward pressure is applied to A relative to C. By reversing the sign of the pressure gradient (i.e. applying higher pressure to C relative to A), the direction of this flow can be reversed, as shown in FIG. 8b.

In FIG. 8b, a flow of at least 4 ml/hour may be achieved between the waste reservoir C and the sample inlet reservoir A. Thus, either a portion or the entire contents of waste reservoir C may be re-analyzed in laser interrogation region 101 to confirm the operation of the particle manipulation device 10. This confirmation reverse flow may be used to adjust the sorting parameters used in system 1000. After a short period of reverse flow, the sorting procedure may resume, using the updated or improved parameters, as was shown in FIG. 8a.

The reverse-flow cytometric confirmation process may be particularly suited to the out-of-plane type of microfabricated valve, shown in FIGS. 8a and 8b. In particular, it has been determined that a microfabricated valve with at least one output channel being disposed out-of-the plane of the sample inlet channel and one other in-plane output channel, may have substantially lower turbulence and reduced resistance to fluid flowing backwards through the device. This applies to reverse-flow confirmation of both the sort and non-sort fraction. The reduced turbulence during valve actuation relative to other actuators, may reduce the likelihood of sorting errors while reversing flow direction in the sort channel. Because of its low resistance to fluid flow, the reverse flow and interrogation may be performed more quickly, and so with less processing overhead that other valve architectures. Accordingly, such an architecture may be particularly advantageous for implementation of the concepts described here.

Figure 9B:
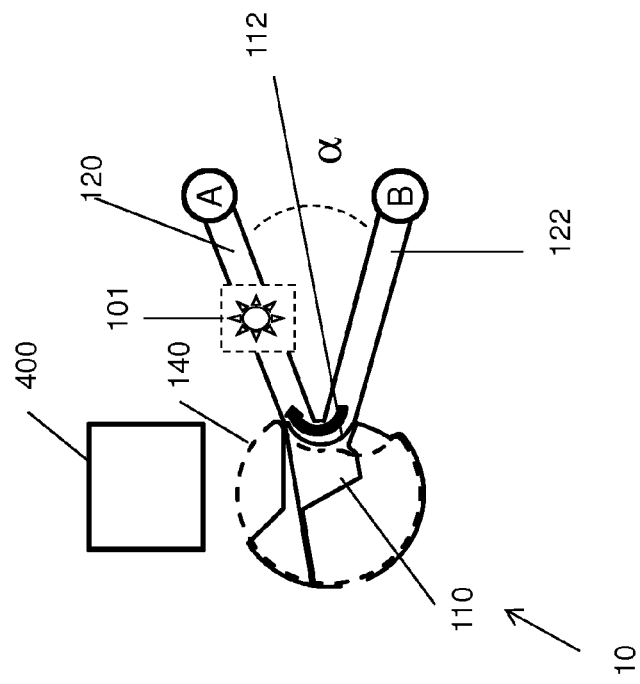
FIG. 9b is a simplified plan view of a microfabricated particle sorting system in the actuated (sort) position and with backward flow and reverse pressure as shown in FIG. 7b.
Figure 9A:
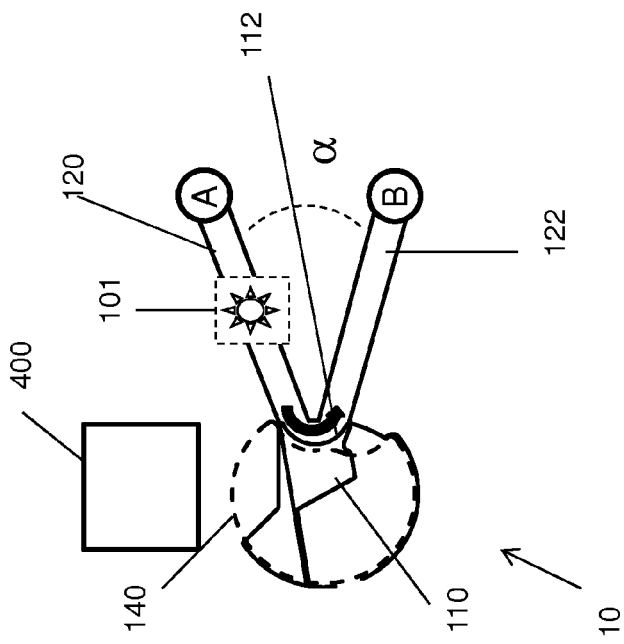

FIG. 9a is a plan view of the particle manipulation device 10 in the actuated position. In this position, the movable member or valve 110 is deflected upward into the position shown in FIG. 2. The diverting surface 112 is a sorting contour which redirects the flow of the inlet channel 120 into the sort output channel 122. The output channel 122 may lie in substantially the same plane as the inlet channel 120, such that the flow within the sort channel 122 is also in substantially the same plane as the flow within the inlet channel 120. There may be an angle α between the inlet channel 120 and the sort channel 122. This angle may be any value up to about 90 degrees. In one embodiment, the angle α between the inlet channel 120 and the sort channel 122 may be about 0, meaning that the flows in the two respective channels are essentially antiparallel. The flow in the waste channel 140 may be substantially orthogonal to flow in the sample inlet channel 120 and the sort channel 122. This arrangement may have advantages in terms of minimizing path lengths within the laser interrogation region and reducing resistance to fluid flow as described previously, and so may improve the accuracy of the device.

Actuation of movable member 110 may arise from a force from force-generating apparatus 400, shown generically in FIGS. 9a and 9b. In some embodiments, force-generating apparatus may be an electromagnet, however, it should be understood that force-generating apparatus may also be electrostatic, piezoelectric, or some other means to exert a force on movable member 110, causing it to move from a first position (FIG. 8a, 8b) to a second position (FIG. 9a, 9b). If electromagnetic forces are used, the effect may be enhanced by the inclusion of a permeable magnetic feature, such as a region of inlaid NiFe permalloy, inlaid in the movable member. Details as to the design and fabrication of such an inlaid permeable feature may be found in the incorporated '095 application. Magnetic forces arising between this permeable feature and force generating apparatus 400, here an external electromagnet, may produce the motion from the first position (FIG. 8a, 8b) to the second position (FIG. 9a, 9b).

More generally, the microfabricated particle manipulation system 10 shown in FIGS. 8a, 8b, 9a and 9b may be formed on a surface of a fabrication substrate, wherein the micromechanical particle manipulation device 10 may include a microfabricated, movable member 110 having a diverting surface 112, wherein the movable member 110 moves from a first position to a second position in response to a force applied to the movable member, wherein the motion is substantially in a plane parallel to the surface, a sample inlet channel 120 formed in the substrate and through which a fluid flows, the fluid including one or more target particles and non-target material, wherein the flow in the sample inlet channel is substantially parallel to the surface. A plurality of output channels 122, 140 may be disposed in the substrate, into which the microfabricated member 110 diverts the fluid. In one embodiment, the flow in at least one output channel 140 is not parallel to the plane but is substantially orthogonal to it, and at least one output channel 140 is located directly below at least a portion of the movable member 110 over at least a portion of its motion.

In one embodiment, the diverting surface 112 may be nearly tangent to the input flow direction as well as the sort output flow direction, and the slope may vary smoothly between these tangent lines. In this embodiment, the moving mass of the stream has a momentum which is smoothly shifted from the input direction to the output direction, and thus if the target particles are biological cells, a minimum of force is delivered to the particles. The angle between the input direction and the output direction is labeled "α" as shown in FIGS. 8a, 8b, 9a and 9b. This angle may be most conveniently between 0 and 90 degrees, and in one embodiment, is essentially 0 degrees, meaning that the flow in the sample inlet channel 120 is substantially antiparallel to the flow in the sort output channel 122.

The microfabricated particle manipulation system 10 may also have a movable member 110 with a diverting surface 112 having a smoothly curved shape, wherein the surface which is substantially tangent to the direction of flow in the sample inlet channel at one point on the shape and substantially tangent to the direction of flow of a first output channel at a second point on the shape, wherein the diverting surface diverts flow from the sample inlet channel into the first output channel when the movable member 110 is in the first position, and allows the flow into a second output channel in the second position. In other words, a passage between the sample inlet channel and a first output channel (i.e., a waste channel) is formed when the particle sorting mechanism is in a first position, and a passage between the sample inlet channel and a second output channel (i.e., the sort channel) is formed when the particle sorting mechanism is in the second position.

In other embodiments, the overall shape of the diverter 112 may be circular, triangular, trapezoidal, parabolic, or v-shaped for example, but the diverter serves in all cases to direct the flow from the inlet channel to another channel.

It should be understood that although channel 122 is referred to as the "sort channel" and orifice 140 is referred to as the "waste orifice", these terms can be interchanged such that the sort stream is directed into the waste orifice 140 and the waste stream is directed into channel 122, without any loss of generality. Similarly, the "inlet channel" 120 and "sort channel" 122 may be reversed. The terms used to designate the three channels are arbitrary, but the inlet stream may be diverted by the valve 110 into either of two separate directions, at least one of which does not lie in the same plane as the other two. The term "substantially" when used in reference to an angular direction, i.e. substantially tangent or substantially vertical, should be understood to mean within 15 degrees of the referenced direction. For example, "substantially orthogonal" to a line should be understood to mean from about 75 degrees to about 105 degrees from the line.

The device shown in FIG. 9a is designed to transport nominally 4 ml of fluid/hour from sample inlet source A to sort reservoir B when the valve is in the position shown in FIG. 9a, and forward pressure is applied to A relative to B. By reversing the sign of the pressure gradient (i.e. applying higher pressure to B relative to A), the direction of this flow can be reversed, as shown in FIG. 9b.

In FIG. 9b, a flow of at least 4 ml/hour may be achieved between the sort reservoir B and the sample inlet reservoir A. Thus, either a portion or the entire contents of sort reservoir B may be analyzed in laser interrogation region 101. The confirmation reverse flow may be used to adjust the sorting parameters. After a short period of reverse flow, the sorting procedure may resume, using the updated or improved parameters, as was shown in FIG. 9a.

Figure 10A:
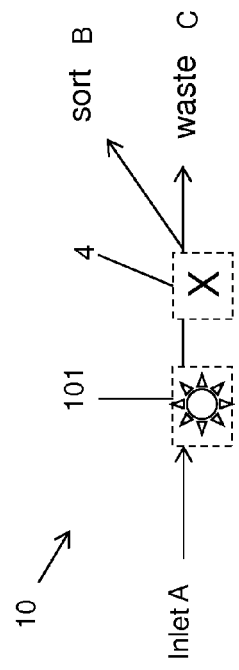
FIG. 10a is a schematic view of a particle sorting system performing a forward sort procedure.
Figure 10B:
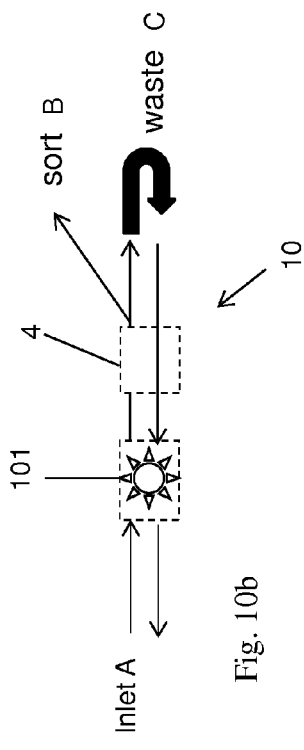
FIG. 10b is a schematic view of a particle sorting system performing a reverse cytometric confirmation from the waste reservoir.
Figure 10C:
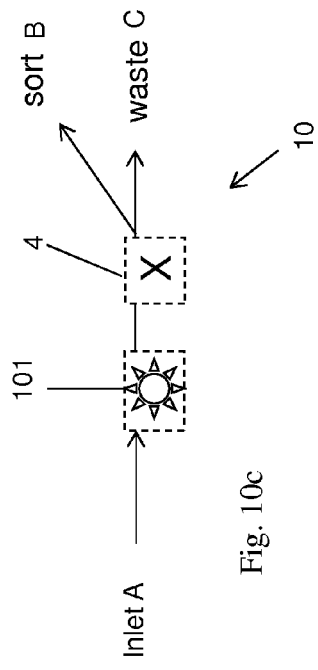
FIG. 10c is a schematic view of a particle sorting system performing a forward sort procedure using parameters from the confirmation.

FIG. 10a-10c shows conceptually the reverse flow/confirmation cytometry described above with respect to FIGS. 8a, and 8b, except that in FIG. 10a-10c, the details of the particle manipulation device 10 are not shown. It should be understood that the concepts described above may be applied to other particle manipulation devices 10 shown generically in FIGS. 10a-10c, and should not be limited to the device shown in FIGS. 8a, and 8b. A pressure control means, or more generally a fluid control means, may be used to control the pressure, and thus the flow, between A, B and C. The control means may be, for example, mechanically pressing on a flexible diaphragm that is in contact with fluid reservoirs A, B and C. For example, pressing harder on reservoir A than reservoir B or C would cause fluid to flow from A and into B or C. Reversing the pressure differential would cause the reverse flow. Alternatively, the control means may be pneumatic or hydraulic, and may include a piston with a pump and associated fluidic passages. The control means may enforce a controlled fluid velocity. The controlled velocity may be held constant by the control means, in one embodiment. Or alternatively, the control means may be based on maintaining a constant event rate, such that the fluid velocity changes as a result of changing sample concentrations due to imperfect mixing or cell death for example. The feedback signal may be, for example, the rate of detection or the width of the detected signal. In any case, the pressure control means may be configured to operate during at least one of the forward flow and the reverse flow, as described further below.

In FIG. 10a, a forward pressure is applied between A, B and C, such that flow is from the sample inlet channel and either sort reservoir B or waste reservoir C. After a period of normal sorting, the flow is reverse as shown in FIG. 10b. In FIG. 10b, the waste reservoir C is being evaluated, such that pressure is reversed between C and A. The flow passes from waste reservoir C, back through MEMS particle manipulation mechanism 4 which is in the "waste" position (FIG. 8b), back through laser interrogation region 101 and back into the sample inlet reservoir A. Depending on the results of this cytometric confirmation, the sort parameters may be adjusted. The period required for this reverse flow and confirmation will depend on the statistics required for the measurement, but may be on the order of seconds to minutes. With adjusted parameters, the sort may be resumed as shown in FIG. 10c. As indicated in FIG. 10a and FIG. 10c, the presence of the "X" in the box indicating the MEMS particle manipulation mechanism 4 indicated that the valve is active, and is at least part of the time in the actuated, sort position as shown in FIGS. 9a and 9b. The absence of the "X" in FIG. 10b indicates that the sample inlet-to-waste path is always open, providing an open path for the backflow of fluid from waste reservoir to sample inlet reservoir, and closing the path to the sort channel B.

Adjustments to the sort purity and/or sort yield can be accomplished by changing one or more of many parameters, including but not limited to:

The duration of time the valve is held open in the second, sorting position, also known as gate duration;

The gate timing (time when the valve is opened after signal detection indicates a sort event);

The fluid flow rate;

The distribution of signals that are used to generate a sort event, also known as sort criteria.

The system may be able to make the sort and yield purity measurements and automatically adjust the purity and yield by adjusting one or more parameters, such as those listed above. This may all take place automatically, via a software algorithm, or by an operator.

FIG. 11a shows conceptually the reverse flow/confirmation cytometry described above with respect to FIGS. 9a and 9b, except that in FIG. 11a-11c, the details of the MEMS device 4 are not shown. It should be understood that the concepts described above may be applied to other MEMS particle manipulation stages 4 shown generically in FIGS. 11a-11c, and should not be limited to the device shown in FIGS. 9a and 9b.

In FIG. 11a, forward pressure is applied between A, B and C, such that flow is from the sample inlet channel and either sort reservoir B or waste reservoir C. After a period of normal sorting, the flow is reversed as shown in FIG. 11b. In FIG. 11b, the sort reservoir B is being evaluated, such that pressure is reversed between B and A. The flow passes from sort reservoir B, back through MEMS particle manipulation mechanism 4 which is in the "sort" position (FIG. 9b), back through laser interrogation region 101 and back into the sample inlet reservoir A. Depending on the results of this cytometric confirmation, the sort parameters may be adjusted. The period required for this reverse flow and confirmation will depend on the statistics required for the measurement, but may be on the order or seconds to minutes. With adjusted parameters, the sort may be resumed as shown in FIG. 11c. As before, the presence of the "X" in the box indicates that the MEMS particle manipulation mechanism 4 is active, and is at least part of the time in the actuated, sort position as shown in FIGS. 9a and 9b. The presence of the "X" in FIG. 11b indicates that the sample inlet-to-sort path is always open, providing an open path for the backflow of fluid from sort reservoir to sample inlet reservoir.

For any particle sorting mechanism, there is an inherent trade-off between sort purity and sort speed. One can only increase the fluid speed to a certain point, after which one runs into physical limitations of the sorter, for example, when the valve speed is such that there is insufficient time to open the valve or flap when a cell is detected. Beyond that limitation, the most obvious way to achieve more events per second is to increase the cell density. But, with increased cell density, the incidence of sort conflicts, wherein both a desired and an undesired cell are collected, also increases.

Figure 15:
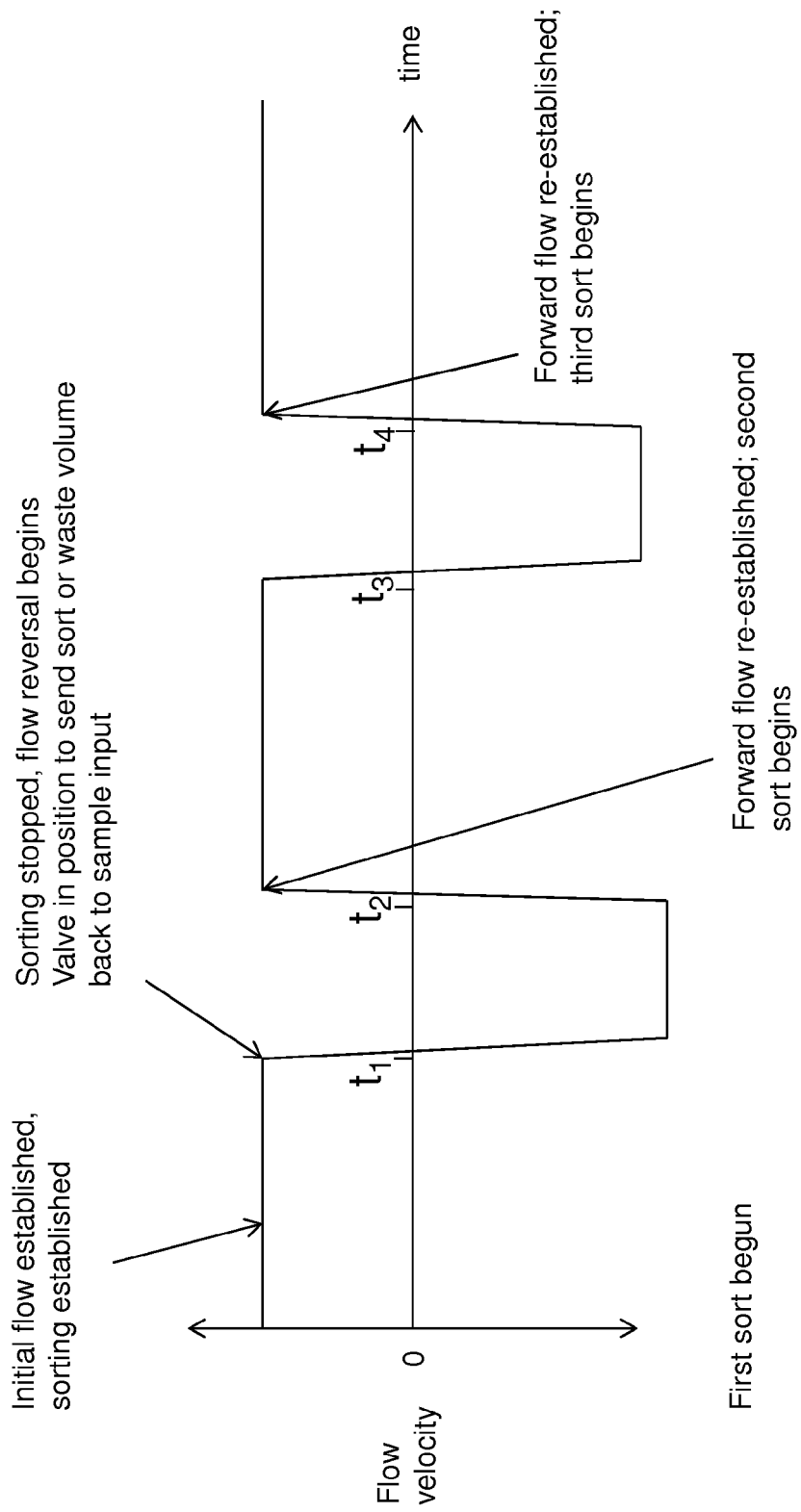
FIG. 15 is a diagram of a control algorithm for a serial sorting routine.

In order to overcome this limitation, a cell sample may theoretically be processed multiple times in a sequential sort strategy—initially a very rapid, crude sort followed by a—slower, high precision sort. This is generally not a practical option with a traditional FACS system as a result of massive cell dilution (from sheath fluid), slow processing speeds and unacceptable cell damage resulting from high pressure electrostatic sorting. A single pass through a flow cytometer is exceptionally violent, with 10 m/sec velocities, explosive decompression from 60 psi to 0 psi. Cells are unlikely to survive such treatment on multiple passes without significant loss of viability. Even if one is willing to accept the dilution, manual processing and cell death, the yield losses on a FACS would be overwhelming, time constant per cycle for processing, cleaning, sterilization and certification is untenable and the sterility of the sample is completely compromised. As a result, this sequential sorting is not practical approach for FACS-based clinical cell sorting. FIGS. 12a, 12b and 15 illustrate how sequential sorting can be carried out using the architecture described herein. Although these figures are described specifically with respect to a sorting process, it should be understood that it may also be applied to other sorts of microfabricated manipulators, such as devices which impart a charge, apply a force, apply a field, apply a high power laser, or otherwise manipulate the particles in the fluid stream.

FIG. 12a shows conceptually the reverse flow-sequential sort process described above with respect to FIGS. 8a, 8b, 9a and 9b, except that in FIGS. 12a and 12b, the details of the MEMS particle manipulation mechanism 4 are not shown. It should be understood that the concepts described above may be applied to other MEMS devices 4 shown generically in FIGS. 12a and 12b, and should not be limited to the device shown in FIGS. 8a, 8, 9a and 9b.

In FIG. 12a, the sorting procedure may be carried out for an extended period before reversing the flow. This period may be sufficient to sort substantially all of the sample fluid, such that a substantial volume of fluid winds up in either the sort reservoir B or the waste reservoir C. At this point, the pressure between waste reservoir C and sample inlet reservoir A is reversed, sending substantially all the contents of the waste reservoir, or any portion thereof, back to the sample inlet reservoir A.

Upon delivering the desired portion of the waste volume to the sample inlet reservoir, the flow is reversed again for normal sorting. As this volume of fluid has already been sorted once, the outcome of the second sort may be to send target cells which were erroneously directed to the waste channel in the first sort, into the proper sort channel on the second sort. This second sort may be expected to improve the overall yield of the sort, by recapturing erroneously sorted particles.

FIG. 12b illustrates another algorithm for sequentially sorting the sorted effluent from the MEMS particle sorting system. As before, the sorting procedure may first be carried out for an extended period or until the sample fluid is exhausted. On completion, the volume of fluid will wind up in either the sort reservoir B or the waste reservoir C. At this point, the pressure between sort reservoir B and sample inlet reservoir A is reversed, sending substantially all the contents of the sort reservoir, or any portion thereof, back toward the sample inlet reservoir A.

Upon delivering the desired portion of the sort volume to the sample reservoir, the flow is reversed again to the forward direction for normal sorting. As this volume of fluid has already been sorted once, the outcome of the second sort may be to improve purity, that is, sending non-target cells which were erroneously directed to the sort channel now to the waste channel on the second sort. This second sort may be expected to improve the overall purity of the sorted output.

Figure 13:
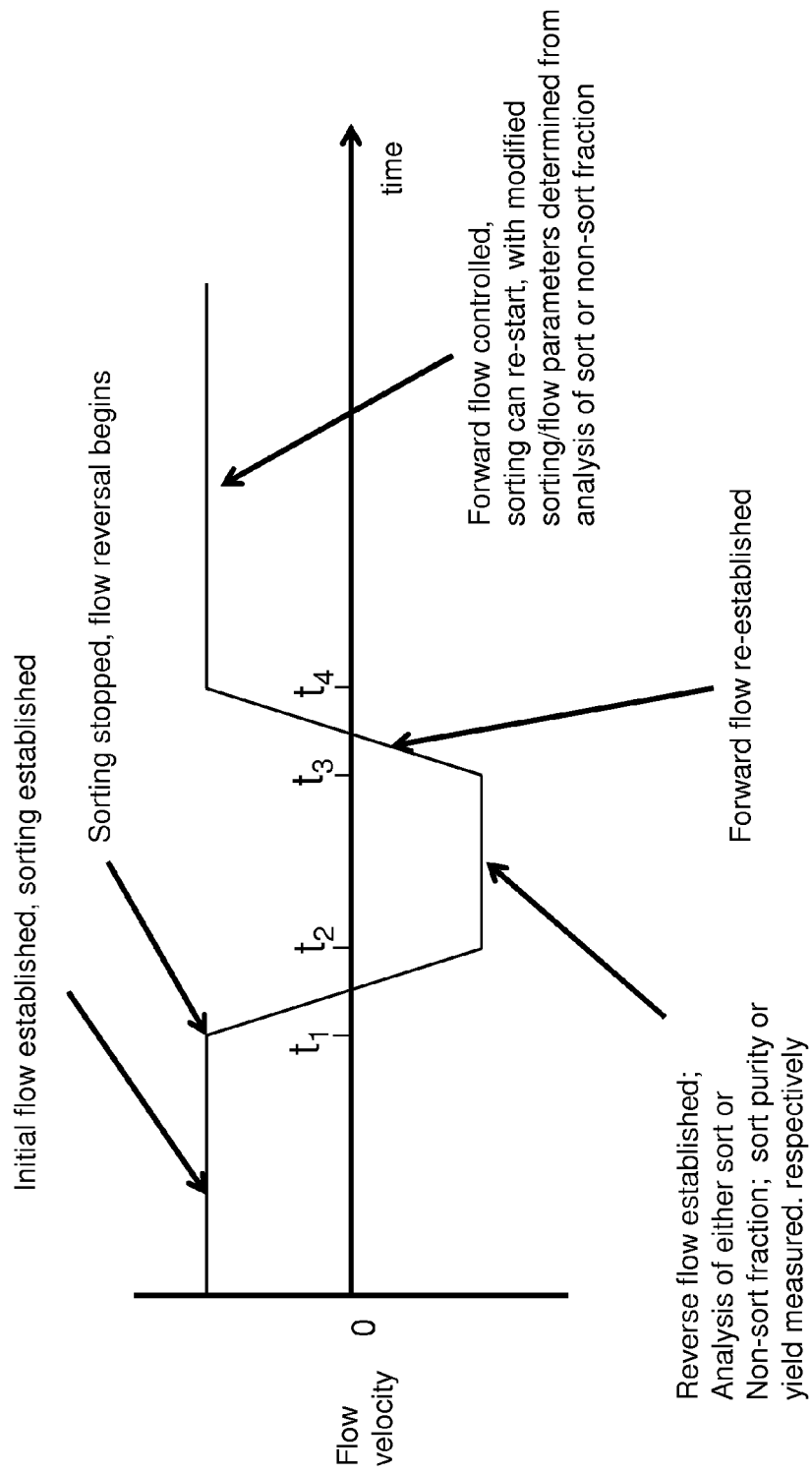
FIG. 13 is a diagram of a control algorithm for a cytometric confirmation of sorting performance in terms of sort purity or sort yield.
Figure 14:
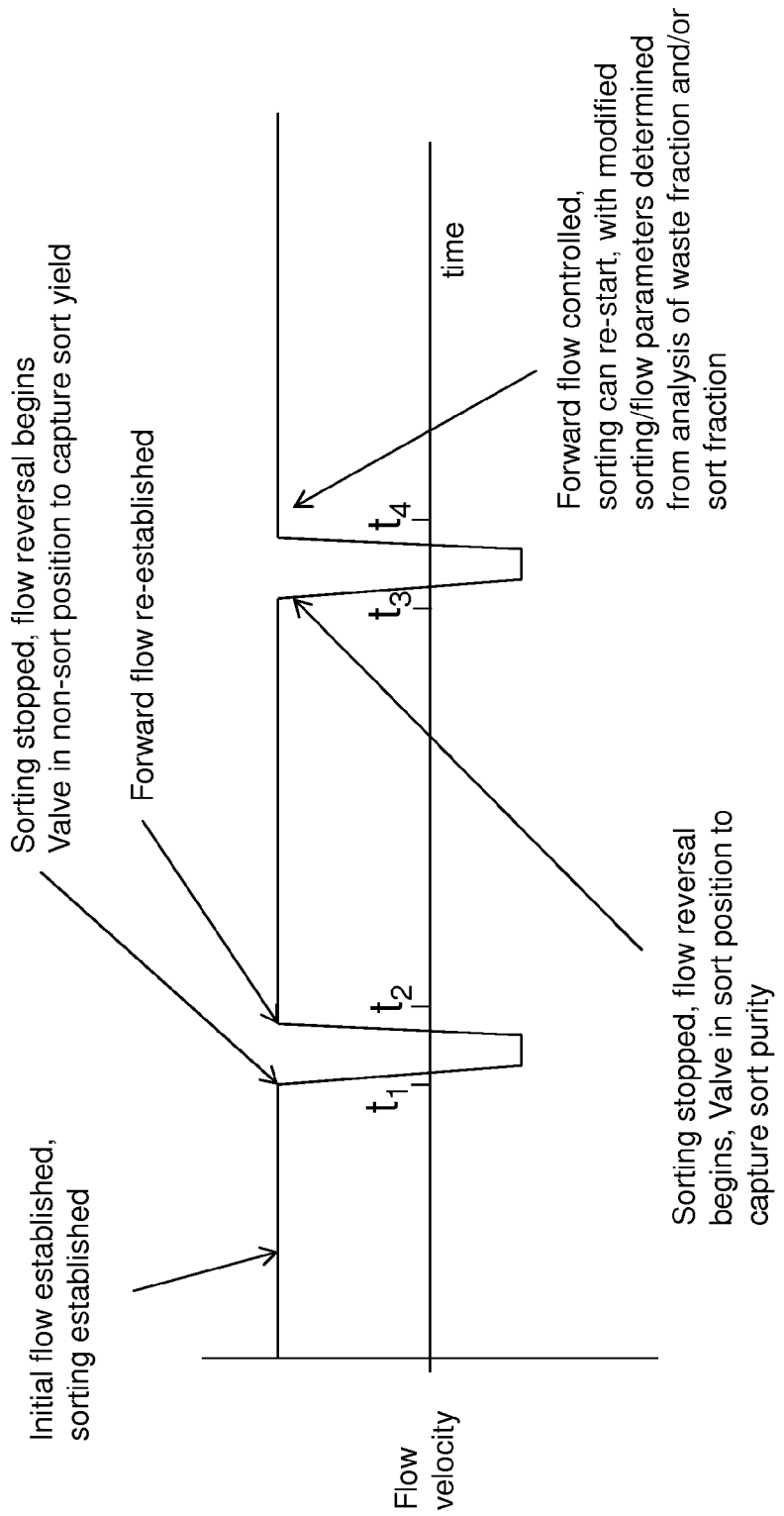
FIG. 14 is a diagram of a control algorithm for a cytometric confirmation of sorting performance in terms of sort purity and sort yield.

FIGS. 13-15 are diagrams of control algorithms for sorting particles in a system with a cytometric confirmation capability as described above. Each of these figures shows the flow velocity on the y-axis (vertical axis) as a function of time on the x-axis (horizontal axis). The units on these axes are not specified, as the diagrams are intended to be qualitative only, illustrating the basic aspects of the algorithms.

FIG. 13 is a diagram of one embodiment of a control algorithm for a cytometric confirmation of sorting performance in terms of sort purity or sort yield, as described above. The figure may illustrate the pressure applied between either the sample inlet reservoir and the sort reservoir, or the pressure between the sample inlet reservoir and the waste reservoir.

For the period of time $t=0$ to $t=t_1$, the pressure differential is positive, meaning that the fluid velocity (y-axis) is positive, and the fluid flows from the sample inlet reservoir to either the sort or waste reservoir. From $t=t_1$ to $t=t_2$ t, the sign of the pressure gradient switches, so that the fluid velocity slows and then reverses. From $t=t_2$ to $t=t_3$, the fluid flows in the opposite direction. The cytometer may measure the number of target particles passing the interrogation region in this period of time. From $t=t_3$ to $t=t_4$, the sign of the pressure differential flips again, and the reverse flow slows and switches direction. At time $t=t_4$, the normal sorting resumes, perhaps with parameters adjusted according to the results collected during the cytometric portion $t=t_2$ to $t=t_3$. The sorting process after $t=t_4$ uses the positive pressure, forward flow as shown in FIG. 13.

With microfabricated channel dimensions on the order of 20 microns, wide enough to comfortably admit a biological cell of interest, single file, flow rates on the order of 1 μl/sec (about 4 ml/hour) may be used. Typical cell concentrations may be on the order of 1M/ml, so that an event rate of 1000 cells/sec may be easily achieved. Accordingly, to achieve statistically significant numbers of events during the reverse flow, the cytometric confirmation routine may require about 10-20 seconds of reverse flow. Most sort processes last on the order of 1 hour, and consume about 4 ml of sample material.

To monitor such a sorting process every 10 minutes, for example, may require only about 1.5 minutes of reverse flow time, for an overhead rate of only about 1.5/60=2.5%.

Accordingly, a method for sorting particles may include providing a sample stream, a sort stream, and a waste stream, all connected by microfluidic channels formed on the surface of a substrate, wherein the sample stream flows from a sample reservoir to at least one of a sort reservoir and a waste reservoir when a flow is forward. It may also include disposing an interrogation means in the sample stream, wherein target particles provide a detection signal when passing through the interrogation means in a first interrogating period, and providing a microfabricated particle sorting mechanism at a junction of the sort stream and waste stream, wherein the microfabricated particle sorting mechanism moves in a plane parallel to the surface, and wherein at least one of the sort stream and the waste stream is substantially orthogonal to the surface. Then the method may include directing the target particles from the sample stream into the sort reservoir based on the detection signals, and directing the other particles into the waste reservoir to sort the particles in a first sorting period. Finally, one may reverse the flow from at least one of the sort reservoir and the waste reservoir back to the sample stream, and back through the interrogation means and the microfabricated particle sorting mechanism. During this period of reverse flow, sorting parameters may be adjusted and the adjusted parameters enforced during ensuing sort periods.

FIG. 14 is a diagram of another embodiment of a control algorithm for a cytometric confirmation of sorting performance in terms of sort yield as well as sort purity. According to this algorithm, sorting again proceeds for the period of time $t=0$ to $t=t_1$, during which the pressure differential is positive, meaning that the fluid velocity (y-axis) is positive, and the fluid flows from the sample inlet reservoir to either the sort or waste reservoir. At $t=t_1$, the sign of the pressure gradient switches between the waste reservoir and the sample inlet reservoir, so that the fluid velocity slows and then reverses. From $t=t_1$ to $t=t_2$, the fluid flows in the opposite direction, from the waste reservoir to the sample inlet reservoir. The movable member or valve 110 may be in the position shown in FIG. 8b, so that a passage is opened between the waste reservoir C and the sample inlet reservoir A. During this period, the cytometer may measure the number of target particles passing the interrogation region to get the waste purity $P_w$. The number of target particle found in the waste flow is indicative of the yield of the sort. That is, sort yield may be defined as the input purity ($P_i$) minus the non-sorted waste purity ($P_w$), divided by the input purity, or yield $Y=(P_i-P_w)/P_i$. Other definitions of sort yield may also be used. The sort parameters may be adjusted to improve this number.

At $t=t_3$, the sign of the pressure gradient switches between the sort reservoir and the sample inlet reservoir, so that the fluid velocity slows and then reverses. From $t=t_3$ to $t=t_4$, the fluid flows in the opposite direction, from the sort reservoir to the sample inlet reservoir. The movable member or valve 110 may be in the position shown in FIG. 9b, so that a passage is opened between the sort reservoir B and the sample inlet reservoir A. During this time, the cytometer may measure the number of non-target particles passing the interrogation region in this period of time. The number of nontarget particle found in the sort flow is indicative of the purity of the sort. That is, the number of target particles ($S_t$) collected divided by the sum of the target particles ($S_t$) collected and nontarget particles ($S_n$) collected, may be defined as the sort purity $P=S_t/(S_t+S_n)$. Other definitions of sort purity may also be used. The sort parameters may be adjusted to improve this number.

At time $t_4$, the sign of the pressure differential flips again, and the reverse flow slows and switches direction. At time $t=t_4$, the normal sorting resumes with positive pressure and forward flow, and perhaps with parameters adjusted according to the results collected during the cytometric portion $t=t_3$ to $t=t_4$. The sorting process after $t_4$ may have improved performance because of the cytometric evaluation period from $t_1$ to $t=t_2$ and $t=t_3$ to $t=t_4$. Accordingly, the interrogation means and microfabricated particle sorting mechanism may configured to detect target particles with the flow reversed from the sort stream to the sample stream, and measures a sort yield. Alternatively or in addition to, the interrogation means and microfabricated particle sorting mechanism may be configured to detect particles with the flow reversed from the waste stream to the sample inlet stream, and measures a sort purity.

It should be understood that although the flow rates for the forward fluid direction and the reverse flow direction, and the duration of these flows, is shown as approximately equal in FIG. 14, this is not necessarily the case. In particular, because the cell concentrations may be substantially different in the sort volume compared to the waste volume, the flow rates may be substantially different as well. Because the statistics of the cytometric confirmation are directly related to the cell concentrations, the duration of each of these confirmation periods may be different as well. Similarly, although FIG. 14 indicates that sorting only begins when the fluid velocity has reached a certain threshold, it should be understood that the sorting can begin prior to this point, with slower velocity, as long as the direction of the flow is as intended. In general, the particle sorting system may be configured such that the sorting mechanism operates during the forward flow to sort the particles, and the interrogation means operates during the reverse flow to count the particles. However, various alternatives may exist, such as disabling the laser interrogation means and/or the particle sorting mechanism during certain periods of the procedure. One such example is illustrated with respect to FIG. 15, described below.

Of course, it should also be understood that the waste reservoir may be analyzed before the sort reservoir, or the sort (or waste) reservoir may be analyzed multiple number of times, rather than the waste reservoir followed by the sort reservoir as described above.

FIG. 15 is a diagram of yet another embodiment of a control algorithm for cytometric confirmation, this time for a serial sorting routine. According to this algorithm, sorting again proceeds for the period of time $t=0$ to $t=t_1$, during which the pressure differential is positive, meaning that the fluid velocity (y-axis) is positive, and the fluid flows from the sample inlet reservoir to either the sort or waste reservoir. At $t=t_1$, the sign of the pressure gradient switches between the sort reservoir and the sample inlet reservoir, so that the fluid velocity slows and then reverses. From $t=t_1$ to $t=t_2$, the fluid flows in the opposite direction, from the sort reservoir to the sample inlet reservoir. During this time, the cytometer may measure the number of target particles passing the interrogation region in this period of time, as in the previous embodiments, or the cytometric function may not be enabled, and during this period, the volume of fluid is simply returned from the sort reservoir to the sample inlet reservoir. With the cytometric confirmation disabled, the fluid velocity during the reverse direction $t=t_1$ to $t=t_2$, may be substantially larger than the fluid velocity in the forward direction, for example, the fluid velocity may be on the order of 10 ml/hour in the reverse direction, but less than about 4 ml/hour in the forward direction.

At $t=t_2$, the sign of the pressure gradient switches again, so that the pressure and flow are again in the forward direction.

Then, from t=t₂ to t=t₃, the fluid is sorted a second time. During this second pass, particles which were erroneously allowed in the sorted fraction may be removed, thus improving the purity of the sorted sample.

Then, at t=t₃, the pressure and flow are again reversed, and the contents of the sort reservoir are returned once more to the sample inlet reservoir. At t=t₄, yet another sorting procedure can be carried out on the sample.

It should also be understood that instead of delivering the contents of the sort reservoir to the sample inlet reservoir, the contents of the waste reservoir may be returned instead, and a second sort carried out on this volume of fluid. In this case, target particles which were missed on the first pass and erroneously sent to the waste reservoir my be returned to the sort reservoir. Using this technique, an essentially arbitrarily high sort yield may be achieved.

While two sequential sorting routines are described here, it should be understood that this concept can be extended to any number of additional sorting procedures, leading to an arbitrarily high sort purity or sort yield. Accordingly, the reversing step and sorting steps may be repeated for a plurality of sorting periods, until at least one of a predefined sort purity or predefined sort yield is achieved.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Accordingly, the exemplary implementations set forth above, are intended to be illustrative, not limiting.

What is claimed is:

1. A particle manipulation system, comprising:
   a sample channel, a sort channel and a waste channel in fluid communication with one another and formed in a surface of a substrate, wherein a flow in the sample channel is substantially parallel to the surface, and wherein the sample channel flows to at least one of the sort channel and the waste channel when the flow is forward;
   an interrogation means disposed in the sample channel, wherein target particles provide detection signals;
   a microfabricated particle sorting mechanism which moves in a plane parallel to the surface, and directs the target particles from the sample channel into the waste channel when the microfabricated particle sorting mechanism is in a first position, and which directs the other particles into the sort channel when in a second position; and
   a fluid control means for controlling a direction and rate of fluid flow in the channels, wherein the fluid control means reverses the flow from at least one of the sort channel and the waste channel back to the sample channel, such that the fluid passes through the interrogation region and the microfabricated particle sorting mechanism a plurality of times
   and wherein the microfabricated particle sorting mechanism moves from the first position to the second position in response to a force, and wherein the motion is substantially in a plane parallel to the surface of the substrate and wherein at least one of the sort channel and the waste channel is substantially orthogonal to the surface and directly below at least a portion of the microfabricated particle sorting mechanism over at least a portion of its motion.

2. The particle manipulation system of claim 1, wherein the particle sorting mechanism has a smoothly curved shape, which is tangent to the input flow direction as well as the sort output flow direction, varies smoothly between these tangent lines.

3. The particle manipulation system of claim 1, wherein flow in the sort channel is substantially antiparallel to flow in the sample channel.

4. The particle manipulation system of claim 1, further comprising:
   a permeable magnetic material inlaid in the microfabricated particle sorting mechanism; and
   a first source of magnetic flux external to the microfabricated particle sorting mechanism and substrate on which the microfabricated particle sorting mechanism is formed, wherein the magnetic flux interacts with the inlaid permeable magnetic material to move the microfabricated particle sorting mechanism, whereby the microfabricated particle sorting mechanism moves from the first position to the second position when the source of magnetic flux is activated.

5. The particle manipulation system of claim 1, wherein the fluid control means comprises at least one of a pneumatic mechanism, a hydraulic mechanism, a piston and a flexible diaphragm.

6. The particle manipulation system of claim 2, wherein the force is at least one of magnetic, electrostatic, and piezoelectric.

7. The particle manipulation system of claim 1, wherein when the microfabricated particle sorting mechanism is in a first position, a passage between the sample channel and the waste channel is formed.

8. The particle manipulation system of claim 1, wherein when the microfabricated particle sorting mechanism is in the second position, a passage between the sample channel and the sort channel is formed.

9. The particle manipulation system of claim 1, wherein the fluid control means reverses the direction of fluid flow with the microfabricated particle sorting mechanism in the first position.

10. The particle manipulation system of claim 1, wherein the fluid control means reverses the direction of fluid flow with the microfabricated particle sorting mechanism in the second position.

11. The particle manipulation system of claim 1, wherein the interrogation means is configured to detect the target particles with the flow reversed from the sort channel to the sample channel, and measures a sort purity.

12. The particle manipulation system of claim 1, wherein the interrogation means is configured to detect the target particles with the flow reversed from the waste channel to the sample channel, and measures a sort yield.

13. The particle manipulation system of claim 1, wherein the fluid control means which is configured to control the flow within the channels according to at least one of a rate of detection signals and a width of detection signals.

14. The particle manipulation system of claim 1, wherein the interrogation means is configured to detect target particles with the flow reversed from the sort channel to the sample channel, and measures a sort purity.

15. The particle manipulation system of claim 1, wherein the interrogation means is configured to detect particles with the flow reversed from the waste channel to the sample channel, and measures a sort yield.

16. The particle manipulation system of claim 6, wherein the microfabricated particle sorting mechanism is configured to operate during the forward flow to sort the particles and the interrogation means is configured to operate during the reverse flow to count the target particles.

17. A method for manipulation particles in a fluid, comprising:
providing a sample stream, a sort stream, and a waste stream, all connected by microfluidic channels formed on the surface of a substrate, wherein the sample stream flows from a sample reservoir to at least one of a sort reservoir and a waste reservoir when a flow is forward;
disposing an interrogation means in the sample stream, wherein target particles provide a detection signal when passing through the interrogation means in a first interrogation period;
providing a microfabricated particle sorting mechanism at a junction of the sort stream and the waste stream, wherein the microfabricated particle sorting mechanism moves in a plane parallel to the surface, and wherein at least one of the sort stream and the waste stream is substantially orthogonal to the surface;
and wherein the microfabricated particle sorting mechanism moves from the first position to the second position in response to a force, and wherein the motion is substantially in a plane parallel to the surface of the substrate and wherein at least one of the sort channel and the waste channel is substantially orthogonal to the surface and directly below at least a portion of the microfabricated particle sorting mechanism over at least a portion of its motion,
directing the target particles from the sample stream into the sort reservoir based on the detection signal, and directing the other particles into the waste reservoir to sort the particles in a first sorting period; and
reversing the flow from at least one of the sort reservoir and the waste reservoir back to the sample stream, to form a reversed stream which flows back through the interrogation means and the microfabricated particle sorting mechanism.

18. The method of claim 17, further comprising:
counting a number of target particles or other particles in the reversed stream during a second interrogation period.

19. The method of claim 18, further comprising:
measuring at least one of a sort purity and a sort yield based on the number of counted particles;
adjusting at least one sorting parameter;
reversing the flow again to pass the sample stream through the interrogation means for a third interrogation period; and
sorting the fluid with the at least one adjusted parameter in second sorting period.

20. The method of claim 17, further comprising:
sorting the fluid from the sample reservoir in a second sorting period, based on the detection signals.

21. The method of claim 20, further comprising:
repeating the reversing and sorting steps for at least one additional sorting period, until at least one of a predefined sort purity or predefined sort yield is achieved.

22. The method of claim 19, wherein the at least one sorting parameter comprises one of gate duration, gate timing, fluid flow rate and sort criteria and the at least one sorting parameter is adjusted based on at least one of the measured sort purity and sort yield.

* * * * *